US007112319B2

(12) United States Patent
Broderick et al.

(10) Patent No.: US 7,112,319 B2
(45) Date of Patent: Sep. 26, 2006

(54) IDENTIFICATION, DIAGNOSIS, AND TREATMENT OF NEUROPATHOLOGIES, NEUROTOXICITIES, TUMORS, AND BRAIN AND SPINAL CORD INJURIES USING MICROELECTRODES WITH MICROVOLTAMMETRY

(75) Inventors: Patricia A. Broderick, Bronx, NY (US); Steven V. Pacia, New York, NY (US)

(73) Assignees: The Research Foundation of the City University of New York, New York, NY (US); New York University, New York, NY (US)

( * ) Notice: Subject to any disclaimer, the term of this patent is extended or adjusted under 35 U.S.C. 154(b) by 276 days.

(21) Appl. No.: 10/118,571

(22) Filed: Apr. 8, 2002

(65) Prior Publication Data

US 2003/0032001 A1 Feb. 13, 2003

Related U.S. Application Data

(60) Provisional application No. 60/282,004, filed on Apr. 16, 2001, provisional application No. 60/297,276, filed on Jun. 11, 2001, provisional application No. 60/326,407, filed on Oct. 1, 2001.

(51) Int. Cl.
*A61K 49/00* (2006.01)

(52) U.S. Cl. ............... 424/9.1; 424/1.11; 424/1.65; 424/9.2

(58) Field of Classification Search ............... 424/1.11, 424/1.65, 9.1, 9.2; 435/4; 600/378
See application file for complete search history.

(56) References Cited

U.S. PATENT DOCUMENTS

| | | | |
|---|---|---|---|
| 4,883,057 A | 11/1989 | Broderick | |
| 5,353,802 A | 10/1994 | Ollmar | 128/734 |
| 5,443,710 A | 8/1995 | Broderick | |
| 5,521,101 A | 5/1996 | Saini et al. | 456/518 |
| 5,569,591 A | 10/1996 | Kell et al. | 435/29 |
| 5,814,991 A | 9/1998 | Deimling | 324/309 |
| 5,938,903 A | 8/1999 | Broderick | |
| 6,235,489 B1 | 5/2001 | Jackoawski | |
| 6,287,452 B1 | 9/2001 | Allen et al. | 205/777.5 |
| 6,321,101 B1 | 11/2001 | Holmstrom | 600/345 |
| 6,321,105 B1 | 11/2001 | Jenkins et al. | |
| 6,402,689 B1 | 6/2002 | Scarantino et al. | 600/300 |

FOREIGN PATENT DOCUMENTS

| | | |
|---|---|---|
| EP | 909143067 | 8/1990 |
| EP | 0487647 | 6/1992 |
| HK | 1007350 | 4/1999 |
| WO | 9102485 | 3/1991 |
| WO | WO 02/082970 | 10/2002 |

OTHER PUBLICATIONS

Schuff N et al., 2002, "Selective reduction of N-acetylaspartate in medial temporal and parietal lobes in AD" Neurology 58(6):928-935.
Lim KO et al., 1999, "Compromised white matter tract integrity in schizophrenia inferred from diffusion tensor imaging" Arch Gen Psychiatry 56(4):367-374.
Lozano AM et al., 1995, "Microelectrode monitoring of cortical and subcortical structures during stereotactic surgery" Acta Neurochir Suppl (Wien) 64:30-34.
Noseworth JH et al., 1988, "Postnatal NMR changes in guinea pig central nervous system: potential relevance to experimental allergic encephalomyelitis" Magn Reson Med 6(2):199-211.
Kataoka K et al., 1987, "Differentiation between cortical and subcortical lesions following focal ischemia in cats by multimodality evoked potentials" J Neurol Sci 79(1-2):117-127.
Frytak S et al., 1985, "Magnetic resonance imaging for neurotoxicity in long-term survivors of carcinoma" Mayo Clin Proc 60(12):803-812.
Ohye C et al., 1984, "Stereotactic CT scan applied to stereotactic thalamotomy and biopsy" Act Neurochir (Wien) 71(1-2):55-68.
Patricia A. Broderick, Mar. 2002, "Microsensors Detect Neuroadaptation by Cocaine: Serotonin Release in Motor Basal Ganglia Is Not Rhythmic with Movement" in Handbook of Neurotoxicology, vol. 2 (Massaro EJ, ed.) Humanna Press, Totowa, NJ, Chapter 13, pp. 323-367.
Pacia S.V. Biogenic amines in the human neocortex in patients with neocortical Biogenic amines in the human neocortex in patients with neocortical and mesial temporal lobe epilepsy: identification with in situ microvoltammetry, Brain Res. Apr. 27, 2001;899(1-2):106-11.

(Continued)

*Primary Examiner*—Dameron L. Jones
(74) *Attorney, Agent, or Firm*—Morgan & Finnegan, LLP

(57) ABSTRACT

The present invention relates to devices and methods of use thereof for making semiderivative voltammetric and chronoamperometric measurements of chemicals, e.g. neurotransmitters, precursors, and metabolites, in vitro, in vivo, or in situ. The invention relates to methods of diagnosing and/or treating a subject as having or being at risk of developing a disease or condition that is associated with abnormal levels of one or more neurotransmitters including, inter alia, epilepsy, diseases of the basal ganglia, athetoid, dystonic diseases, neoplasms, Parkinson's disease, brain injuries, spinal cord injuries, and cancer. The invention provides methods of differentiating white matter from grey matter using microvoltammetry. In some embodiments, regions of the brain to be resected or targeted for pharmaceutical therapy are identified using Broderick probes. The invention further provides methods of measuring the neurotoxicity of a material by comparing Broderick probe microvoltammograms of a neural tissue in the presence and absence of the material.

20 Claims, 10 Drawing Sheets

OTHER PUBLICATIONS

Broderick, P.A., Pacia, S.V., Doyle, W.K. and Devinsky, O., 2000, Monoamine neurotransmitters in resected hippocampal subparcellations from neocortical and mesial temporal lobe epilepsy patients: in situ microvoltammetric studies. Brain Res. 878:48-63.

Broderick, P.A., 2000, Serotonin (5-HT) deficiency but high tryptophan (L-TP) concentrations within hippocampal subparcellations in patients with mesial temporal sclerosis (MTS). Amer. Epilepsy Soc. Los Angeles, CA, Epilepsia 41(Suppl.):91.

Morgan, P.T., Perrins, R., Lloyd, P.E. and Weiss, K.R., 2000, Intrinsic and extrinsic modulaton of a single central pattern generating circuit. J. Neurophysiol. 84:1186-1193.

Pearson, K. and Gordon, J., 2000, Locomotion, in Principles of Neural Science (Kandel, E.R., Schwartz, J.H. and Jessell, T.M., eds.), 4th edition, The McGraw Hill Companies, Inc., NY, pp. 738-755.

Allen, S.M. and Davis, W.M., 1999, Relationship of dopamine to serotonin in the neonatal 6-OHDA rat model of Lesch-Nyhan Syndrome. Behav. Pharmacol. 10:467-474.

Broderick, P.A., Jean-Baptiste, P., Vuong, A.V., Pacia, S.V., Doyle, W.K. and Devinsky, O., 1999, Neurochemical signals from living neocortex of Mesial Temporal Lobe Epilepsy (MTLE) patients studied by Broderick Probe® lauric acid and stearic acid miniature sensors. Epilepsia (Suppl.7) 40:78-79.

Stokes, A.H., Hastings, T.G., Vrana, K.E., 1999. Cytotoxic and Genototic Potential of Dopamine. J. Neurosci. Res. 55:659-665.

Arshawsky, Y.I., Deliagina, T.G., Orlovsky, G.N., Panchin, Y.V., Popova, L.B. and Sadreyev, R.I., 1998, Analysis of the central pattern generator for swimming in the mollusk, Clione. Ann. NY Acad. Sci. 860:51-69.

Bordey, A., Sontheimer, H., 1998. Properties of human glial cells associated with epileptic seizure foci. Epilepsy Res. 32:286-303.

Broderick, P.A. and Piercey, M.F., 1998, Clozapine, haloperidol, and the D4 antagonist, PNU-101387G: in vivo effects on mesocortical, mesolimbic, and nigrostriatal dopamine and serotonin release. J. Neural. Transm. 105:749-767.

Guertin, P.A. and Hounagaard, J., 1998, Chemical and electrical stimulation induce rhythmic motor activity in an in vitro preparation of the spinal cord from adult turtles. Neurosci. Lett. 245:5-8.

Katz, P.S., 1998, Neuromodulation intrinsic to the central pattern generator for escape swimming in Tritonia. Ann. NY Acad. Sci. 860:181-188.

Y. Kawaguchi and T. Shindou, 1998, Noradrenergic excitation and inhibition of GABAergic cell types in rat frontal cortex, J Neurosci 18:6963-6976.

Lucki, I., 1998, The spectrum of behaviors influenced by serotonin. Biol. Psychiat. 44:151-162.

Martin, P., 1998, 5-HT2 Receptor Antagonism and Antipsychotic Drugs; A Behavioral and Neurochemical Study in a Rodent Hypoglutamatergia Model. PhD. Thesis, Goteborg Univ., Sweden, pp. 1-64.

Sadamoto, H., Hatakeyama, D., Kojima, S., Fujito, Y. and Ito, E., 1998, Histochemical study on the relation between NO-generative neurons and central circuitry for feeding in the pond snail, Lymnaea Stagnalis. Neurosi. Res. 32:57-63.

Abi, Dargham, A., Laruelle, M., Aghajanian, G.K., Charney, D. and Krystal, J., 1997, The role of serotonin in the pathophysiology and treatment of schizophrenia. J. Neuropsychiat. Clin. Neurosci. 9:1-17.

Broderick et al., 1997, "A Four Week Follow-Up Study Of Serotonin (5-Ht) And Dopamine (Da) Release In Nucleus Accumbens Of Animals Behaving In An Open-Field Paradigm" Society for Neurosci Abstract 23:1867.

Broderick PA and FelixCF, 1997, "Serotonin (5-HT) Within Dopamine Reward Circuits Signals Open-field Behavior. II. Basis for 5-HT-DA Interaction in Cocaine Dysfunctional Behavior" Neuroscience and Biobehavioral Reviews 21(3):227-260.

W.K. Doyla and D.D. Spencer, Anterior temporal resections. In: Epilepsy: A comprehensive textbook. eds J Engel Jr. and TA Pedley. Lippincott-Raven Publishers, Philadelphia (1997) 1807-1815.

S.V. Pacia and J.S. Ebersole, 1997, Intracranial EEG substrates of Scalp ictal patterns from temporal lobe foci, Epilepsia 38:642-654.

Yeghiayan, S.K., Kelley, A.E., Kula, N.S., Campbell, A. and Baldessarini, R.J., 1997, Role of dopamine in behavioral effects of serotonin microinjected into rat striatum. Pharmacol. Biochem. Behav. 56:251-259.

Brooks DJ, 1996, Basal Ganglia function during normal and Parkinsonian movement, PET activation studies, In Advances in Neurology (Battistin, L. Scarlato, G., Caraceni, T. and Ruggieri, S. Eds.), Lippincott-Raven, Phil. PA. pp. 433-441.

Kapur, S. and Remington, G., 1996, Serotonin-dopamine interaction and its relevance to schizophrenia. Am. J. Psychiat. 153(4):466-476.

Kiehn, O. and Kjaerulff, O., 1996, Spatiotemporal characteristics of 5-HT and dopamine-induced rhythmic activity in the in vitro neonatal rat. J. Neurophysiol. 75:1472-1482.

Kissinger, P.T., Preddy, C.R., Shoup, R.E. and Heineman, W.R., 1996, Fundamental concepts o analytical electrochemistry, in Laboratory Techniques in Electroanalytical Chemistry (Kissinger, P.T. and Heineman, W.R., eds.), Marcell Dekker Inc., NY, pp. 11-50.

D.G. MacGregor, hI.J. Higgins, P.A. Jones, et al., 1996, Ascorbate attenuates the the systemic kainate-induced neurotoxicity in the rat hippocampus, Brain Res. 727:133-144.

S.V. Pacia, O. Devinsky, K. Perrine, et al., 1996, Clinical features of neocortical temporal Lobe epilepsy, Ann Neurol 40:724-730.

E. Schlicker, K. Fink, J. Zentner, et al., 1996, Presynaptic inhibitory serotonergic autoreceptors in human hippocampus, Naunyn Schmiedebergs Arch Pharmacol. 354:393-396.

Wadenburg, M.L., 1996, Serotonergic mechanisms in neuroleptic-induced catalepsy in the rat. Neurosci. Biobehav. Rev. 20:325-339.

Hope, O., Lineen, E., Okonji, C., Green, S., Saleem, A., Aulakh, C.S. and Broderick, P.A., 1995 Cocaine has remarkable nucleus accumbens effects on line, with behavior in the serotonin-deficient Fawn Hooded rat. NIH/NIGMS Symposium, Washington, D.C.

Iqbal, N. and van Praag, H.M., 1995, The role of serotonin in schizophrenia. Eur. Neuropsychopharmacol. 5(Suppl.):11-23.

M.R. Pranzatelli, E. Tate, Y. Huang, et al., 1995, Neuropharmacology of progressive myoclonu epilepsy: response to 5-hydroxy-L-tryptophan, Epilepsia; 36:783-791.

Katz, P.S., Getting, P.A. and Frost, W.N., 1994, Dynamic neuromodulation of synaptic strength intrinsic to a central pattern generator circuit. Nature 367:729-731.

J.H. Meador-Woodruff, DK Grandy, HH Van Tol, et al., 1994, Dopamine receptor gene expression in the human medial temporal lobe, Neuropsychopharmacology 10:239-248.

Z. Radisavljevic, C. Cepeda, W Peacock W et al., 1994, Norepinephrine modulates excitatory amino acid-induced responses in developing human and adult rat cerebral cortex, International Journal of Developmental Neuroscience 12:353-361.

Rossignol, S. and Dubue, R., 1994, Spinal pattern generation. Curr. Opin. Neurobiol. 4:894-902.

P.A. Broderick, 1993, In vivo electrochemical studies of gradient effects of (sc) cocaine on dopamine and serotonin release in dorsal striatum of conscious rats, Pharmacol. Biochem. Behav. 46:973-984.

M.J. During, and D.D. Spencer, 1993, Extracellular hippocampal glutamate and spontaneous seizure in the conscious human brain, Lancet 341:1607-1610.

Kimelberg, H.K., Jalonen, T., Walz, W., 1993. Regulation of the brain microenvironment: Transmitters and ions. In: Murphy, S. (Ed.), Astrocytes, Pharmacology and Function. Academic Press, San Diego, CA, pp. 193-228.

Neal-Beliveau, B.S., Joyce, J.N. and Lucki, I., 1993, Serotonergic involvement in haloperidol-induced catalepsy. J. Pharmacol. Exp. Therap. 265:207-217.

Jacobs, B.L. and Azmitia, E.C., 1992, Structure and function of the brain serotonin system. Physiol. Rev. 72:165-229.

Barbeau, H. and Rossignol, S., 1991, Mitigation and modulation of the locomotor pattern in the adult chronic spinal rat by noradrenergic and dopaminergic drugs. Brain Res. 546:250-260.

Jacobs, B.L. and Fornal, C.A., 1991, Activity of brain serotonergic neurons in the behaving animal. Pharmacol. Rev. 43:563-578.

Lehmann, and A. Hamberger, Extracellular levels of amino acids in epilepsy: Methods and Findings. In Neurotransmitters and epilepsy eds. Fischer RS and Coyle JT. Wiley-Liss, (1991) pp. 167-180.

Trent, F. and Tepper, J.M., 1991, Dorsal raphe stimulation modifies striatal-evoked antidromic invasion of nigral dopaminergic neurons in vivo. Exp. Brain Res. 84:620-630.

Van Tol, H.H.M., Bunzow, J.R., Guan, H.C., Sunuahara, R.K., Seeman, P., Niznik, H.B. and Civello, O., 1991, Cloning of the gene for human dopamine D4 receptor with high affinity for the antipsychotic clozapine. Nature 350:610-614.

Broderick, P.A., 1990, State-of-the-art microelectrodes for in vivo voltammetry. Electroanalysis 2:241-251.

Hollermann, J.R. and Grace, A.A., 1990, The effects of dopamine-depleting brain lesions on the electrophysiological activity of rat substantia nigra dopamine neurons. Brain Res. 533:203-212.

M. Pintor, I.N. Mefford, .1 Hutter, et al., 1990, Levels of biogenic amines, their metabolites, and tyrosine hydroxylase activity in the human epileptic temporal cortex, Synapse 5:152-156.

Stoecker, P.W. and Yacynyck, A. M., 1990, Chemically modified electrodes as biosensors. Selective Electrode Rev. 12:137-160.

Teitelbaum P, Pellis SM, and De Vietti TL, 1990, Disintegration into sterotypy induced by drug of brain damage: a microdescriptive behavioral analysis. In: Neurobiology of Sterotyped Behavior (Cooper SJ and Dourish CT Eds.), Oxford Univ. Press, NY. pp. 169-199.

Broderick, P.A., 1989, Characterizing stearate probes in vitro for the electrochemical detection of dopamine and serotonin. Brain Res. 495:115-121.

R.A. Browning, D.R. Wade, M. Marcinczyk, et al., 1989, Regional brain abnormalities in norepinephrine uptake and dopamine beta-hydroxylase activity in the genetically epilepsy prone rat, J Pharmacol Exp Ther 249:229-235.

M. Cams, R. Cortes, B. Gueye, et al., 1989, Dopamine receptors in the human brain: autoradiographic distribution of D2 sites, Neuroscience 28:275-290.

Coury, L.A., Huber, E.W. and Heineman, W.P., 1989, Applications of modified electrodes in th voltammetric determination of catecholamine neurotransmitters. Biotechnology 11:1-37.

Hillegaart, V., Wadenberg, M.L. and Ahlenius, S., 1989, Effects of 8-OH-DPAT on motor activity in the rat. Pharmacol. Biochem. Behav. 32:797-800.

W. Janusz and Z. Kleinrok, 1989, The role of the central serotonergic system i n pilocarpine-induced seizures: receptor mechanisms, Neurosci Res 7:144-153.

M. Levine, W. Hartzell, K. Dhariwal et al., Ascorbic acid regulation i n norepinephrine biosynthesis In situ. In Molecular biology of Stress. Alan R. Liss Inc. (1989) pp. 191-201.

Meltzer, H.Y., 1989, Clinical studies on the mechanism of action of clozapine: the dopamine-serotonin hypothesis of schizophrenia. Psychopharmocology 99(Suppl.):18-27.

Ribeiro-Do-Valle, L.E., Fornal, C.A., Litto, W.J. and Jacobs, B.L., 1989, Serotonergic dorsal raphe unit activity related to feeding/grooming behaviors in cats. Soc. Neurosci. Abstr. 15:1283.

Walz, W., 1989. Role of glial cells in the regulation of brain microenvironment. Prog. Neurobiol. 33:309-333.

Broderick PA, 1988, Distinguishing in vitro electrochemical signatures for norepinephrine and dopamine, Neurosci. Lett. 95:275-280.

D.S. Goldstein, N.S. Nadi, R. Stull, et al., 1988, Levels of catechols in epileptogenic and nonepileptogenic regions of the human brain, J Neurochem 50:225-229.

Kane, J., Honigfeld, G., Singer, J. and Meltzer, H., 1988, Clozapine for the treatment resistant schizophrenic. A double-blind comparison with chlorpromazine. Arch. Gen. Psychiat. 45:789-796.

Grillner, S., Wallen P., Dale, N., Brodin, I., Buchanan, J. and Hill, R., 1987, Transmitter, membrane properties and network circuitry in the control of locomotion in the lamprey. Trends Neurosci. 10:34-41.

Tamminga, C.A. and Gerlach, J., 1987, New neuroleptics and experimental antipsychotics in schizophrenia, in Psychopharmacology: the Third Generation of Progress (Meltzer, H.Y., ed.), Raven Press, NY, pp. 1129-1140.

Altar, C.A., Wasley, A.M., Neale, R.F. and Stone, G.A., 1986, Typical and atypical antipsychotic occupancy of D2 and S2 receptors: an autoradiographic analysis in rat brain. Brain Res. Bull. 16:517-525.

Azmitia, E.C., 1986, Re-engineering the brain serotonin system: localized application of neurotoxins and fetal neurons. Adv. Neurol. 43:493-507.

J.A. Ferrendelli, 1986, Role of biogenic amines and cyclic nucleotides in seizure mechanisms, Adv. Neurol. 44:393-400.

Jacobs, B.L., 1986, Single unit activity of brain monoamine containing neurons in freely movin animals, in Neurochemical Analysis of the Conscious Brain: Voltammetry and Push-Pull Perfusion (Myers, R.D. and Knott, P.J., eds.), Ann. NY Acad. Sci., pp. 70-79.

RA. Akiyama, T. Kat, K. Ishii, and E. Yasud, 1985, In vitro measurement of dopamine concentration with carbon fiber electrodes, Anal Chem. 57:1518-1522.

Grace, A. and Bunney, B.S., 1985, Dopamine, in Neurotransmitter Actions in the Vertebrate Nervous System (Rogawski, M.A. and Barker, J.L., eds.), Plenum Press, NY, Chapter 9, pp. 127-128.

Harris-Warrick, R.M. and Cohen, A.H., 1985, Serotonin modulates the central pattern generator for locomotion in the isolated lamprey spinal cord. J. Exp. Biol. 116:27-46.

A.V. Delgado-Escueta, 1984, The new wave of research in the epilepsies, Ann Neurol. 16(suppl.):145-158.

Doudet, D., Gross, C., Seal, G. and Bioulac, B., 1984, Activity of nigral dopaminergic neurons after lesion of the neostriatum in rats. Brain Res. 302:45-55.

H.E. Laird, J.W. Dailey, P.C., 1984, Jobe, Neurotransmitter abnormalities in genetically epileptic rodents, Fed Proc. 43:2505-9.

Llinas, R., Greenfield, S.A. and Jahnsen, H., 1984, Electrophysiology of pars compacta cells in the in vitro substantia nigra: a possible mechanism for dendritic release. Brain Res. 294:127-132.

Adams, R.N. and Marsden, C.A., 1982, Electrochemical detection methods for monoamine measurements in vitro and in vivo. in Handbook of Psychopharmacology (Iversen, L.L. and Snyder, S.H., eds.), Plenum Press, NY, pp. 1-74.

Dayton, M.A., Brown, J.C., Stutts, K.J. and Wightman, R.M., 1980, Faradaic electrochemistry a microvoltammetric electrodes. Anal. Chem. 52:946-950.

McCall, R.B. and Aghajanian, G.K., 1980, Pharmacological characterization of serotonin receptors in the facial motor nucleus: a microiontophoretic study. Eur. J. Pharmacol. 65:175-183.

Patten, J., 1980, Neurological Differential Diagnosis. Harold Starke Limited, London and Springer-Verlag Inc., NY, pp. 127-128.

McCall, R.B. and Aghajanian, G.K., 1979, Serotonergic facilitation of facial motor neuron excitation. Brain Res. 169:11-27.

Schlosberg, A.J. and Harvey, J.A., 1979, Effects of L-dopa and L-5-hydroxytryptophan on locomotor activity of the rat after selective or combined destruction of central catecholamine an serotonin neurons. J. Pharmacol. Exp. Therap. 211:296-304.

Kohler, C. and Lorens, S.A., 1978, Open field activity and avoidance behavior following serotonin depletion: a comparison of the effects of parachlorophenylalanine and electrolytic midbrain raphe lesions. Pharmacol. Biochem. Behav. 8:223-233.

Bouhuys, A.L. and Van den Hoofdakker, R.H., 1977, Effects of midbrain raphe destruction on sleep and locomotor activity in rats. Physiol. Behav. 19:535-541.

Lorens, S.A., Guldberg, H.C., Hole, K., Kohler, C. and Srebro, B., 1976, Activity, avoidance learning and regional 5-hydroxytryptamine following intrabrain stem 5,7-dihydroxytryptamine and electrolytic midbrain raphe lesions in the rat. Brain Res. 108:97-113.

Srebro, B. and Lorens, S.A., 1975, Behavioral effects of selective midbrain raphe lesions in the rat. Brain Res. 89:303-325.

P.T. Kissinger, J.B. Hart, R.N. Adams, 1973, Voltammetry in brain tissue- a neurophysiological measurement. Brain Res 55:209-213.

Oldham, K., 1973, Semi-integral electroanalysis: analog implementation. Anal. Chem. 45:39-50.

Snyder, S.H., 1972, Catecholamines in the brain as mediator of amphetamine psychosis. Arch. Gen. Psychiat. 27:169-179.

Jankowska, E., Jukes, M.G.M., Lund, S. and Lundberg, A., 1967a, The effect of DOPA on the spinal cord. 5. Reciprocal organization of pathways transmitting excitatory action to alpha motoneurones of flexors and extensors. Acta Physiol. Scand. 70:369-388.

Jankowska, E., Jukes, M.G.M., Lund, S. and Lundberg, A., 1967b, The effect of DOPA on the spinal cord. VI. Half-centre organization of interneurons transmitting effects from flexor reflex afferents. Acta Physiol. Scand. 70:389-402.

Gaddum, J.H., 1954, Drug antagonistic to 5-hydroxytryptamine, in Ciba Foundation Symposium on Hypertension (Wolstenholme, G.W., ed.), Little, Brown, Boston, MA, pp. 75-77.

Wooley, D.W. and Shaw, E., 1954, A biological and pharmacological suggestion of certain mental disorders. Proc. Natl. Acad. Sci. USA:40:228-231.

IDENTIFICATION, DIAGNOSIS, AND TREATMENT OF NEUROPATHOLOGIES, NEUROTOXICITIES, TUMORS, AND BRAIN AND SPINAL CORD INJURIES USING MICROELECTRODES WITH MICROVOLTAMMETRY

This application claims priority to U.S. Application Nos. 60/282,004 filed on Apr. 6, 2001, 60/297,276 filed on Jun. 11, 2001, and 60/326,407 filed on Oct. 1, 2001, all of which are incorporated herein in their entirety by reference.

This invention was made, in part, with government support. The government has certain rights in the invention.

BACKGROUND OF THE INVENTION

The present invention relates to devices and methods of use thereof for determining the presence and concentration of chemicals in a cell, tissue, organ or organism. The invention relates to, inter alia, semiderivative voltammetric measurements and chronoamperometric measurements of chemicals, e.g. neurotransmitters, precursors and metabolites, to identify, diagnose, and/or treat neuropathologies, neurotoxicities, tumors, and brain and spinal cord injuries.

Microvoltammetric indicator microelectrodes pass small but measurable currents while neurotransmitters and metabolites close to the microelectrode surface undergo oxidation and/or reduction (Adams R N et al., 1982, Handbook of Psychopharmacology, pp. 1–74). When an electrode is placed in contact with a solution a phase boundary is created that separates identical solutes into two different types. They are (a) molecules that are at a distance from the microelectrode and (b) those molecules that are close enough to participate in mutual interactions between the surface of the microelectrode and the sample solution interface (Kissinger P T et al., 1996, Laboratory Techniques in Electroanalytical Chemistry, pp. 11–50). Collectively, these interactions are called electrochemistry.

Detection of electrochemical signals from solutions and from anatomic brain sites is termed "faradaic" because the amount of the oxidative and/or reductive species detected at the surface of the microelectrode may be calculated by a derivation of Faraday's Law, the Cottrell Equation, $$i_t = \frac{nFAC_0 D_0^{1/2}}{3.14^{1/2} t^{1/2}}$$

wherein i is current at time t, n is the number of electrons (eq/mol), F is Faraday's constant (96,486 C/eq), A is electrode area (cm$^2$), C is concentration of oxygen (mol/cm$^3$), and D is the diffusion coefficient of oxygen (cm$^2$/s). The proportionality between charge and mass of an electrochemical reaction describes the relationship between the charge of each neurochemical in the process of oxidation and/or reduction and the concentration of each neurochemical. The Cottrell Equation relates to quiet solution experiments wherein the potential is instantaneously switched from an initial value $E_i$ to a final potential, then held constant for a fixed time, then switched back to $E_i$. If material diffuses to a planar electrode surface in only one direction (linear diffusion) then the exact description of the current-time curve is the Cottrell Equation.

Current-time relationships with a circular electrode are defined in electrochemistry by the Cottrell Equation. For a long time, other electrode sizes and experiments using different electrolysis times were considered deviations from the Cottrell Equations that could be considered negligible. However, Wightman et al. observed that linear diffusion is not enough to describe the action that takes place at spherical microelectrodes (Dayton M A et al., 1980, Anal. Chem. 52:948–950). The quiet solution behavior of very small electrodes is different and is better described by a steady state equation in which the radius of the electrode is taken into account (Adams R N et al., 1982, Handbook of Psychopharmacology, pp. 1–74). This equation is suitable for calculating the edge effect or spherical steady-state contribution for even a 300-micron diameter electrode. Such a calculation reveals that the edge effect or spherical steady-state contribution adds approximately 30% current to the linear diffusion component for an electrolysis time of only one second (Dayton M A et al., 1980, Anal. Chem. 52:948–950).

Microvoltammetric circuits using several types of stearate-carbon paste microelectrodes have been developed and refined (Broderick P A, 1995, U.S. Pat. No. 5,433,710; Broderick P A, 1996, EP 90914306.7; Broderick P A, 1999, U.S. Pat. No. 5,938,903). Reliable separation and quantification of neurotransmitters including norepinephrine, serotonin, and dopamine as well as some of their precursors and metabolites is now possible (Broderick P A, 1989, Brain Res. 495:115–121; Broderick P A, 1988, Neurosci. Lett. 95:275–280; Broderick P A, 1990, Electroanalysis 2:241–245).

One electrode for in vivo electrochemical studies was developed in the laboratory of Ralph Adams (Kissinger P T et al., 1973, Brain Res 55:209). Using carbon paste electrodes with diameters reaching 1.6 mm and Ag/AgCl (3M NaCl) reference electrodes, neurotransmitters including dopamine and norepinephrine and their metabolites were detected (not separated), as a single peak in rat caudate nucleus with finite current electrochemistry and cyclic voltammetry.

Extensive refinements to microelectrodes and to in vivo electrochemistry have been made (Broderick P A, 1990, Electroanalysis 2:241–245). The recent development of a stearate-carbon paste probe along with an electrode conditioning process has resulted in reliable separation and detection of norepinephrine, dopamine, and serotonin (Broderick P A, 1996, EP 90914306.7; Broderick P A, 1999, U.S. Pat. No. 5,938,903). In addition, other types of microelectrodes with increased sensitivity and reliability continue to be developed (Broderick P A, 1996, EP 90914306.7; Broderick P A, 1999, U.S. Pat. No. 5,938,903). An electrochemically pre-treated carbon fiber electrode allows the differentiation of dopamine from DOPAC (Akiyama R A et al., 1985, Anal Chem. 57:1518), as do microelectrodes used in the instant invention.

Previous in vitro analysis techniques have yielded disappointing results. Prior ex vivo studies attempted to circumvent these problems with the microdialysis technique (During M J et al., 1993, Lancet 341:1607–1610; Lehmann A et al., 1991, Neurotransmitters and Epilepsy, pp. 167–180). Dialysis tubing placed on or within the brain is perfused with artificial CSF or Krebs-Ringer bicarbonate solution, and the perfusate is then analyzed with High Performance Liquid Chromatography (HPLC) with electrochemical detection; this provides information about the extracellular environment. However, this technique has been criticized because of the local gliosis caused by the dialysis probes and the perfusion process that can alter the biochemical parameters under study. In addition, the perfusate is analyzed outside the brain and therefore in contrast to microvoltammetry measurements are not truly in situ or in vivo.

Epilepsy is a neurological disorder characterized by transient electrical disturbances of the brain that may be studied by electrophysical techniques. Neurotransmitter data from experimental epilepsy models and in vitro analysis of surgically resected specimens from patients with partial epilepsy have thus far yielded conflicting results. These conflicting results may be due to significant variations between samples as well as choice of controls. Additionally, highly localized changes in epileptic cortex are not detectable using whole tissue homogenates. In general, increased activity in noradrenergic, dopaminergic, and serotonergic systems are believed to reduce cortical excitability and decrease seizure activity (Delgado-Escueta A V, 1984, Ann Neurol. 16(Suppl.): 145–148). However, human temporal lobe epilepsy is a complex disorder that may involve the dysfunction of distinct neuronal systems including the hippocampus and entorhinal cortex, the temporal neocortex, or combinations of these structures. Therefore, the contribution of different neurotransmitter systems to epileptogenesis in a given patient likely varies with lesion location and the etiology of epilepsy. Furthermore, recent studies demonstrating presynaptic inhibitory serotonin autoreceptors,-in hippocampus (Schlicker E et al., 1996, Naunyn Schmiedebergs Arch Pharmacol. 354:393–396) and a dual role for norepinephrine in epileptogenesis (Radisavljevic Z et al., 1994, International Journal of Developmental Neuroscience 12:353–361) suggest an even more complex situation.

Recent studies are now defining a syndrome of neocortical temporal lobe epilepsy that has distinct clinicopathologic and electrophysiologic features from mesial temporal lobe epilepsy (Pacia S V et al., 1997, Epilepsia 38:642–654; Pacia S V et al., 1996, Ann Neurol 40:724–730). While both mesial temporal lobe epilepsy and neocortical temporal lobe epilepsy are potentially treatable with surgical resection when seizures are refractory to antiepileptic medication, the type and extent of temporal lobe resection necessary to achieve a seizure free outcome may differ. Neocortical temporal lobe epilepsy patients may require resections tailored to include the epileptogenic zone. These resections may lie outside the boundaries of a standard temporal lobe resection performed for mesial temporal lobe epilepsy. Neurochemistry using microvoltammetry may provide a means for defining the epileptogenic zone in these patients.

Other techniques for detecting neurotransmitters in real time and in vivo fall short of the instant invention. These previous methods such as dialysis have limitations such as those described in During M J et al., 1993, Lancet 341: 1607–1610; Ferrendelli J A et al., 1986, Adv. Neurol. 44:393–400; Goldstein D S et al., 1988, J Neurochem 50:225229; Janusz W et al., 1989, Neurosci Res 7:144153; Kawaguchi Y et al., 1998, J Neurosci 18:6963–6976.

In vivo detection of neurotransmitters and other chemicals is also important for diagnosing and treating movement disorders such as spinal cord injuries and brain injuries. Current techniques are limited, in part, in their relative inability to monitor neural chemistry in real time in a freely behaving animal or human which may limit their diagnostic and/or therapeutic efficacy. Movement may be generated by a central pattern generator (CPG), i.e. a neuronal network capable of generating a rhythmic pattern of motor activity either in the presence or absence of phasic sensory input from peripheral receptors.

Central pattern generators have been identified and analyzed in more than fifty rhythmic motor systems and CPG's can generate a variety of motor patterns. A universal characteristic of this wide variety of motor patterns is that they consist of rhythmic and alternating motions of the body or appendages. It is the rhythmicity of these behaviors that make these behaviors appear stereotypic. It is the repetitive quality of these behaviors that enables stereotypic behaviors to be controlled automatically. This automaticity or autoactivity means that there may be little or no need for intervention from higher brain centers when the environment remains stable.

The simplest CPG's contain neurons that are able to burst spontaneously. Such endogenous bursters can drive other motor neurons and some motor neurons are themselves, endogenous bursters. Importantly, bursters are common in CPG's that produce continuous rhythmic movement, such as locomotion. But, locomotion is an episodic, rhythmic behavior and thus, further regulation by neurochemicals becomes necessary. Endogenous bursts (cell firing) of neurons involved in locomotion must be regulated by neurotransmitters and neuromodulators, i.e., substances that can alter the cellular properties of neurons involved in CPG's. Brief depolarizations occur and lead to maintained depolarizations (plateau potentials) that can last for long periods of time. These maintained depolarizations far outlast the initial depolarization and it is these maintained depolarizations that are necessary for rhythmic movements. The generation of rhythmic motor activity by CPG's can be altered by amines and peptides (Grillner S et al., 1987, Trends Neurosci. 10:34–41; Rossignol S et al., 1994, Curr. Opin. Neurobiol. 4:894–902), thereby enabling a CPG to generate an even greater variety of repetitive motor patterns. Motor CPG's produce a complex temporal pattern of activation of different groups of motor functions and each pattern can be divided into a number of distinct phases even within a phase. CPG's are time-dependent (Pearson K et al., 2000, Principles of Neural Science, 4th edition, pp. 738–755).

Serotonin is an important neuromodulator for CPG's and can control the CPG underlying the escape swim response in the mollusc, *Tritonia diomedea*. The dorsal swim interneurons (DSI'S) are a bilaterally represented set of three 5-HTergic neurons that participate in the generation of the rhythmic swim motor program. Serotonin from these CPG neurons is said to function as both a fast neurotransmitter and as a slower neuromodulator. In its modulatory role, 5-HT enhances the release of neurotransmitter from another CPG neuron, C2 and also increases C2 excitability by decreasing spike frequency adaptation. Serotonin intrinsic to the CPG may neuromodulate behavioral sensitization and habituation. Serotonin intrinsic to the DSI enhances synaptic potentials evoked by another neuron in the same circuit (Katz P S, 1998, Ann. NY Acad. Sci. 860:181–188; Katz P S et al., 1994, Nature 367:729–731).

In another mollusc, the pteropod *Clione limacina,* the CPG for swimming is located in the pedal ganglia and formed by three groups of interneurons which are critical for rhythmic activity. The endogenous rhythmic activity of this CPG was enhanced by 5-HT (Arshavsky Y I et al., 1998, Ann. NY Acad. Sci. 860:51–69). In the pond snail, *Lymnaea stagnalis,* 5-HT is the main neurotransmitter in its stereotypic feeding circuit (Sadamoto H et al., 1998, Lymnaea Stagnalis. Neurosi. Res. 32:57–63). In the sea slug, *Aplysia*, the CPG for biting is modulated both intrinsically and extrinsically. Intrinsic modulation has been reported to be mediated by cerebral peptide-2 (cp-2) containing CB1–2 interneurons and is mimicked by application of CP-2, whereas extrinsic modulation is mediated by the 5-HT-ergic metacerebral cell (MCC) neurons and is mimicked by application of 5-HT (Morgan P T et al., 2000, J. Neurophysiol. 84:1186–1193).

In vertebrates, the 5-HT somatodendritic nuclei, the raphe, comprise the most expansive and complex anatomic and neurochemical system in CNS. Raphe nuclei almost exclusively reside along the midline in the rat and in the primate. Fewer reside along the midline, but several exhibit a paramedian organization (Azmitia E C, 1986, Adv. Neurol. 43:493–507). The rostral 5-HT raphe group and caudal linear nucleus sends 5-HT efferents to $A_9$ basal nuclei motor systems and the caudal 5-HT group, whereas the interfascicular aspect of the 5-HTergic dorsal raphe projects efferents to $A_{10}$ basal ganglia (nuclei) regions (Jacobs B L et al., 1992, Physiol. Rev. 72:165–229).

Electrophysiological studies have shown that the most prominent action of increased 5-HT cell firing, in 5-HT somatodendrites in treadmill locomotion for example, is to increase the flexor and extensor burst amplitude of 5-HT cell firing in dorsal raphe, (DR) somatodendrites for 5-HT, during locomotion (Barbeau H et al., 1991, Brain Res. 546:250–260). Further evidence for 5-HT controlling motor output is seen from studies in which 5-HT, directly injected into the motor nucleus of the trigeminal nerve, increased the amplitude of both the tonic electromyogram of the masseter muscle and the externally elicited jaw-closure (masseteric) reflex (McCall R B et al., 1979, Brain Res. 169:11–27; McCall R B et al., 1980, Eur. J. Pharmacol. 65:175–183; Ribeiro-Do-Valle L E et al., 1989, Soc. Neurosci. Abstr. 15:1283). In fact, Jacobs and Azmitia have proposed that 5-HT's primary function in CNS neuronal circuitry is to facilitate motor output (Jacobs B L et al., 1992, Physiol. Rev. 72:165–229).

Serotonin neurons within 5-HT somatodendrites depolarize with such extraordinary regularity that they exhibit automaticity, i.e., they can act by a CPG and produce plateau potentials. Thus, 5-HT neurons exhibit repetitive discharge characteristics. Increased 5-HT neuronal cell firing in somatodendritic raphe nuclei generally precedes the onset of movement or even increased muscle tone in arousal by several seconds and is maintained during sustained behavior (Jacobs B L, 1986, Neurochemical Analysis of the Conscious Brain: Voltammetry and Push-Pull Perfusion, Ann. NY Acad. Sci., pp. 70–79). Importantly, 5-HT cell firing in raphe nuclei is sometimes phase-locked to repetitive behavioral stereotypic responses. The regular firing of 5-HT somatodendrites in raphe nuclei is activated preferentially. This activation is associated with locomotion and chewing, stereotypic behaviors that are stimulated by CPG's (Jacobs B L et al., 1991, Pharmacol. Rev. 43:563–578). Serotonin intrinsic CPG's have been reported to be responsible for inducing rhythmic motor activity in the spinal cord of the turtle and the lamprey (Guertin P A et al., 1998, Neurosci. Lett. 245:5–8; Harris-Warrick R M et al., 1985, J. Exp. Biol. 116:27–46). The evidence in the lamprey suggests that 5-HT may have a role in the generation of a family of related undulatory movements, including, swimming, crawling, and burrowing, by a single CPG.

In addition to neurological disorders and injuries, the device and methods of use provided herein may be used for for brain cancer diagnosis and treatment. Current imaging technology is limited with respect to tumor visualization in neural tissue. For example, magnetic resonance imaging MRI is limited in its ability to detect tumor infiltration into white matter. This may hinder a physician's ability to render a diagnosis and/or prognosis. It further limits the ability to treat the patient by, for example, hindering a surgeon from defining tumor boundaries to remove the tumor. Alternatively, an inability to visualize cancerous cells or tissue in white matter may hinder a physicians ability to monitor the efficacy of a chemotherapy regimen.

SUMMARY OF THE INVENTION

The present invention relates to devices and methods for microvoltammetric and/or chronoamperometric imaging of temporal changes in neurotransmitter concentrations in living humans and non-human animals comprising contacting cells with a Broderick probe, applying a potential to said Broderick probe, and generating a temporally resolved microvoltammogram. The method may further comprise determining from said microvoltammogram the presence and concentration of at least one marker selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide. Methods of the invention may further comprise comparing the microvoltammogram and/or neurotransmitter concentrations to reference a microvoltammogram and/or neurotransmitter concentration(s).

The present invention relates to devices and methods of use thereof for determining the presence and concentration of chemicals in a cell, tissue, organ or organism. The invention relates to, inter alia, semiderivative voltammetric measurements and chronoamperometric measurements of chemicals, e.g. neurotransmitters, precursors, and metabolites. The invention relates to methods of diagnosing and/or treating a subject as having or being at risk of developing a disease or condition that is associated with abnormal levels of one or more neurotransmitters including, inter alia, epilepsy, diseases of the basal ganglia, athetoid, dystonic diseases, neoplasms, Parkinson's disease, brain injuries, spinal cord injuries, and cancer. Microvoltammetry methods of the invention may be performed in vitro, in vivo, or in situ. The invention provides methods of differentiating white matter from grey matter using microvoltammetry. In some embodiments, the invention provides methods of brain tumor diagnosis using distinct white matter voltammetric signals as detected by Broderick probes. The methods of the invention may be applied to cancer diagnosis and treatment, even where a tumor has infiltrated other tissue, e.g. white matter. In some embodiments, the invention provides methods of treating a tumor wherein the tumor's position is determined using microvoltammetry. The invention relates to use of Broderick probes to determine the concentration of a material, e.g. dopamine, norepinephrine, and serotonin, in the brains of patients having epilepsy. In some embodiments of the invention, regions of the brain to be resected are identified using Broderick probes. In some embodiments of the invention, regions of the brain to be targeted for pharmaceutical therapy are identified using Broderick probes. The invention further provides methods of measuring the neurotoxicity of a material by comparing Broderick probe microvoltammograms of a neural tissue in the presence and absence of the material.

The present invention relates to devices and methods for treating epilepsy. More specifically, the invention relates to use of Broderick probes to ascertain neurotransmitter levels in the brains of patients having epilepsy, especially temporal lobe epilepsy. In some embodiments of the invention, regions of the brain to be resected are identified using Broderick probes. In some embodiments of the invention, regions of the brain to be targeted for pharmaceutical therapy are identified using Broderick probes.

The present invention also relates to devices and methods for reliably distinguishing temporal lobe gray matter from white matter using Broderick probes with microvolatammetry. The invention further relates to methods of brain cancer diagnosis using distinct white matter voltammetric signals as detected by Broderick probes. The invention further relates to diagnosis of other white matter diseases. Nonlimiting examples of white matter diseases are multiple sclerosis, leukodystrophies, mitochondrial diseases, lipid disorders and glial cell-related disorders whether these glial cells or glia are normal, abnormal, modified or cultured and the like.

The present invention further relates to devices and methods for diagnosing and treating cocaine psychomotor stimulant behaviors. In some embodiments of the invention microelectrodes may be contacted with a subject to ascertain changes in neurotransmitter levels, e.g. due to release and/or reuptake, in real time. In some embodiments, the invention provides methods of predicting the occurrence of movement disorder effects of a drug. Nonlimiting examples of movement disorders are cocaine addiction, Huntington's disease, Parkinson's disease, Autism, Lesch-Nyhan Disease and the like.

The present invention further provides devices and methods for diagnosing pathologies and/or abnormalities of neurotransmitter levels. Neurotransmitters that may be detected by the techniques of the invention may be selected from the group consisting of serotonin (5-HT), dopamine (DA), ascorbic acid (AA), norepinephrine (NE), γ-aminobutyric acid (GABA), glutamate, neurotensin, somatostatin, dynorphin, homovanillic acid, uric acid (UA), tryptophan, tyrosine, nitrous oxide, and nitric oxide.

DETAILED DESCRIPTION OF THE INVENTION

Broderick probe—a microelectrode comprising graphite, oil, and a material selected from the group consisting of glycolipids, lipoproteins, saturated and unsaturated fatty acids, and perfluorosulfonated materials. A non-limiting example of a Broderick probe may be found in FIG. 1. Further details and examples may be found in U.S. Pat. Nos. 4,883,057, 5,443,710, and 5,938,903, all to P. A. Broderick including circuit diagrams and methods of making Broderick probes. Broderick probes may be in electrical contact with an auxiliary electrode and/or a reference electrode. It will be apparent to those of ordinary skill in the art, particularly in view of the cited patent documents, that "Broderick probe" is a term that relates to a number of microelectrodes that vary by composition and the type of circuit in which it is employed and that these variations give rise to differences in detection properties.

Broderick probes are miniature carbon-based sensors that are able to detect electrochemical signals for a vast number of neurotransmitters, neuromodulators and metabolites, including neuropeptides, hormones and vitamins (Broderick P A, 1989, U.S. Pat. No. 4,883,057; Broderick P A, 1995, U.S. Pat. No. 5,433,710; Broderick P A, 1997, EP 0487647 B1; Broderick P A, 1999, U.S. Pat. No. 5,938,903; Broderick P A, 1999, Hong Kong, HK # 1007350). These probes have made it possible to routinely and selectively detect in discrete neuroanatomic substrates of living human and animal brain, the monoamines, DA, NE, and 5-HT, in addition to the precursor to 5-HT, 1-tryptophan (1-TP), ascorbic acid (AA) and uric acid (UA) (Broderick P A, 1988, Neurosci. Lett. 95:275–280; Broderick P A, 1989, Brain Res. 495: 115–121; Broderick P A, 1990, Electroanalysis 2:241–251; Broderick P A, 2000, Epilepsia 41(Suppl.):91; Broderick P A et al., 2000, Brain Res. 878:49–63). It is also possible to differentiate catecholamines, DA and NE, electrochemically using these probes (Broderick P A, 1988, Neurosci. Lett. 95:275–280; Broderick P A, 1989, Brain Res. 495:115–121; Broderick P A, 1990, Electroanalysis 2:241–251; Broderick P A, 2000, Epilepsia 41(Suppl.):91; Broderick P A et al., 2000, Brain Res. 878:49–63). More recently, it has been found that these probes are also capable of electrochemical detection of somatostatin and dynorphin A (Broderick P A, 2000, Epilepsia 41(Suppl.):91).

Figure 1:
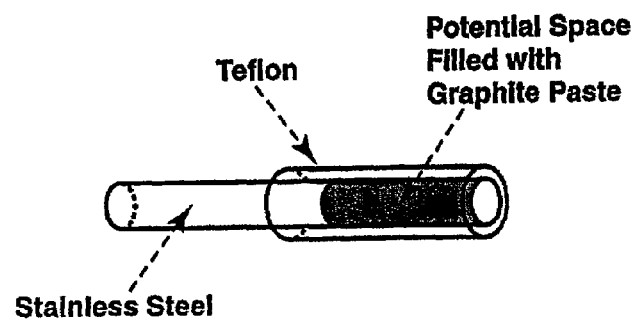
FIG. 1. Schematic diagram of the Broderick probe microelectrodes for the selective electrochemical detection, in vitro, in vivo, and in situ, of neurotransmitters, neuromodulators, metabolites, precursors and peptides in humans and animals, centrally and peripherally. Diagram of microelectrode is greatly oversized; actual sizes range from numbers of microns in single digits to a few hundred microns.
Figure 2:
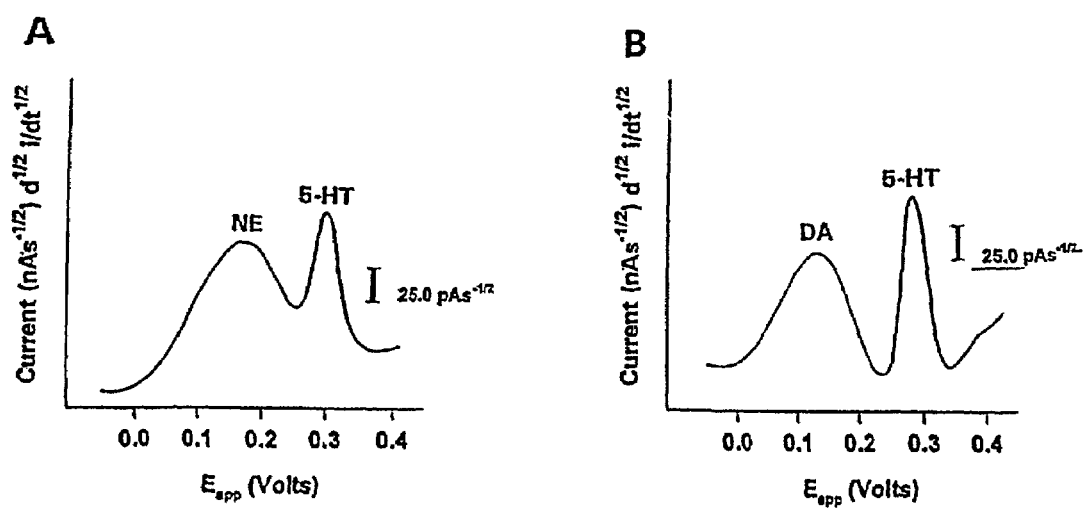
FIG. 2. A and B show semiderivative voltammograms from mesial temporal lobe epilepsy patients #8, and neocortical temporal lobe epilepsy patient #14, when the indicator microelectrode was placed in anterolateral temporal neocortex. The potential applied to the indicator microelectrode in millivolts is plotted on the x-axis. The current derived from each monoamine is plotted on the y-axis. The electrochemical signals are plotted and the characteristic oxidative potentials for each neurotransmitter were identified. Mesial temporal lobe epilepsy patient #8 exhibited the norepinephrine and serotonin signature on the voltammogram at peak oxidation potentials of 0.17V for norepinephrine and 0.305V for serotonin. Neocortical temporal lobe epilepsy patient #14 exhibited dopamine and serotonin signals on the voltammogram at peak oxidation potentials of 0.115V for dopamine and 0.295V for serotonin. Data are drawn from the original voltammogram, recorded in situ, i.e., actual raw data are presented.

In some embodiments of the invention, the Broderick probe is a Broderick probe microelectrode as shown in the schematic diagram in FIG. 1. Within the field of electrochemistry, this sensor is termed the indicator microelectrode and is also called the working microelectrode. The surface of the microelectrode consists of carbon-base and is the electrochemical device.

Broderick probes do not promote bacterial growth either before or after sterilization with gamma irradiation. Gamma irradiation treatment was performed by Sterigenics International, Inc., Haw River, N.C.

Broderick probes can be used effectively for different applications in human and animal surgery. Preliminary studies with Broderick probe stearic versus lauric acid microelectrodes in vitro, in situ, and in vivo showed a possible advantage for the lauric acid microelectrodes for use short-term, e.g., intraoperative recordings, and a possible advantage for stearic acid for use long-term, e.g., chronic monitoring in humans and animals (Broderick P A, 1989, U.S. Pat. No. 4,883,057; Broderick P A, 1995, U.S. Pat. No. 5,433,710; Broderick P A, 1997, EP 0487647 B1; Broderick P A, 1999, U.S. Pat. No. 5,938,903; Broderick P A, 1999, Hong Kong, HK #1007350; Hope O et al., 1995, Cocaine has remarkable nucleus accumbens effects on line, with behavior in the serotonin-deficient Fawn Hooded rat. NIH/ NIGMS Symposium, Washington, D.C.).

Broderick probes can detect basal (normal, natural, endogenous or steady state) concentrations of neurotransmitters and other neurochemicals in vivo, in situ and in vitro. They can also detect alterations in these neurotransmitters or neurochemicals in brain, or body before and after pharmacological manipulation with drugs or other compounds. Neurochemicals during actual, induced or even mimicked brain diseases can be detected as well. Example 5 focuses on 5-HT alterations in NAcc in freely moving animals during normal open-field behaviors of locomotor (exploratory) and stereotypy compared with, in the same animal, cocaine psychomotor stimulant effects on 5-HT and behavior.

Changing the surface of the sensor changes the capacitance of the surface of the sensor. The surface of the indicator microelectrode is a capacitance diffuse double layer ($C_{dl}$) that allows potential to accumulate on its surface. Capacitance is a critical aspect of charging (background)

current. Charging current is a current pulse that flows through the $C_{dt}$ to allow faradaic electron transfer to begin. Accumulation of potential on the surface of the indicator microelectrode is necessary for faradaic electron transfer. Charging current is proportional to electrode surface area; therefore, these miniature sensors (200 microns and less in diameter) minimize charging current effects.

Broderick probes can be used in conjunction with classical electrical circuits used in electrochemistry such as chronoamperometry, differential pulse voltammetry and double differential voltammetry. Another electrical circuit for providing an output signal having a mathematical relationship in operation to an input signal can be semiderivative or semidifferential. These two terms are used interchangeably here, although these two circuits have some technical differences. Semiderivative electroanalysis diminishes non-faradaic current by the addition of analysis time. In the present studies, a CV 37 detector (BAS, West Lafayette, Ind.) was equipped with a semiderivative circuit. This circuit uses a linear scanning methodology as its basis. Semiderivative treatment of voltammetric data means that the signals are recorded mathematically as the first half derivative of the linear analog signal. A semiderivative circuit combines an additional series of resistors and capacitors, called a "ladder network" (Oldham,K, 1973, Anal. Chem. 45:39–50) with the traditional linear scanning technology which then allows more clearly defined waveforms and peak amplitudes of electrochemical signals than was previously possible with linear scanning methodology.

Broderick probe microvoltammogram—These may be plotted as current versus time or as current versus applied potential. Other renderings are also possible. The concentration of biogenic amines and other materials may be deduced from these microvoltammograms, e.g. according to the Cottrell equation. According to the invention, a microvoltammogram is broadly defined as any rendering of the signals from a Broderick probe susceptible to human perception including, but not limited to, paper, electronic, and virtual representations of the Broderick probe signal. An individual of sufficient skill in the art to perceive a Broderick probe signal in real-time, e.g. from a visual display screen, is also within the contemplation and scope of this definition.

The main strength of in vivo microvoltammetry (electrochemistry) is that it allows the study of the neurochemical time course of action of normal neurochemistry, as well as the neurochemistry after an administered drug regimen. Temporal resolution is fast, in seconds and milliseconds. Moreover, the attendant microspatial resolution is superior (availability of discrete areas of brain without disruption). Both highly sensitive temporal and spatial resolution makes these studies ultimately most efficient for mechanism of action studies Another strength lies in the fact that these in vivo microvoltammetric studies are done in the freely moving and behaving animal model, using the same animal as its own control (studies in the living human brain are underway as well). Thus, a direct determination of whether or not a neurochemical effect is abnormal can be made because the normal neurochemical effect is seen a priori.

The basic in vivo electrochemistry experiment involves the implantation of an indicator electrode in a discrete and specified region of brain, the application of a potential to that electrode, the oxidation or reduction of the selected neurochemical and the recording of the resultant current. In essence, the potential is applied between the indicator and the reference electrode; the reference electrode provides a relative zero potential. This is an electrochemical technique with which information about an analyte, a neurotransmitter, or its metabolite, including its concentration, is derived from an electrochemical current as a function of a potential difference. This potential difference is applied to the surface of an electrochemical electrode.

In microvoltammetry, each neurotransmitter, metabolite, precursor to neurotransmitter, etc. is identified by the peak oxidation potential, or half-wave potential at which the neurochemical generates its maximum current. Using the Broderick Probe stearic acid microelectrode inserted in NAcc, the oxidation potential at which DA generates its maximum current in vivo (physiological pH, 37.5° C.) was empirically determined to be +0.140 V (SE ±0.015 V) in over one thousand studies. The oxidation potential at which serotonin generates its maximum current under the same conditions was empirically determined to be +0.290 V (SE±0.015 V) in over one thousand studies.

What matters in microvoltammetry is that each of these biogenic amines have amine groups that are protonated at neutral pH and therefore, exist as cations, whereas metabolites of the monoamines are deprotonated at neutral pH and exist as anions (Coury L A et al., 1989, Biotechnology 11:1–37). Thus, the monoamine metabolites such as the metabolites of DA, 3, 4 dihydroxyphenylacetic acid, (DOPAC), 3,4-dihydroxyphenylglycol (DHPG-DOPEG) and homovanillic acid (HVA) cannot interfere with the detection of DA at the same peak oxidation potential or half-wave potential, characteristic for DA.

The same principles are applicable to detection of the biogenic amine, 5-HT. Serotonin is detected without interference at the same oxidation potential or half-wave potential from either its metabolite, 5-hydroxyindoleacetic acid (5-HIAA) or UA, which is a constituent of brain with similar electroactive properties to those of 5-HT. Factors such as the significantly lower sensitivity of the indicator microelectrode to anions, the charge and diffusion characteristics of each catecholamine or indoleamine vis-à-vis its metabolites, preclude such interference. Descriptions of each neurochemical detected by this inventor with Broderick probes are published in detail (Broderick P A, 1995, U.S. Pat. No. 5,433,710; Broderick P A, 1996, EP 90914306.7; Broderick P A, 1999, U.S. Pat. No. 5,938,903; Broderick P A, 1989, Brain Res. 495:115–121; Broderick P A, 1988, Neurosci. Lett. 95:275–280; Broderick P A, 1990, Electroanalysis 2:241–245; Broderick P A, 1993, Pharmacol. Biochem. Behav. 46:973–984; Broderick P A, 2002, Handbook of Neurotoxicology, Vol. 2, Chapter 13; Broderick P A et al., 2000, Brain Res. 878:48–63; Broderick P A et al., 1997, Neuroscience and Biobehavioral Reviews 21(3):227–260; Broderick P A, 1989, U.S. Pat. No. 4,883,057; Broderick P A, 1997, EP 0487647 B1; Broderick P A, 1999, Hong Kong, HK #1007350; Broderick P A, 2000, Epilepsia 41(Suppl.): 91).

An important distinction between the detection of signals in microvoltammetry as compared with the detection of signals in microdialysis is that in microvoltammetry, the indicator microelectrode is the detecting device, whereas in microdialysis methods, the dialysis membrane is a membrane and not the detecting device. The microdialysis membrane is simply a membrane through which perfusate is collected. The perfusate is then brought to the high performance liquid chromatography (HPLC) device, equipped with an electrochemical column that is the actual detecting device. These electrochemical columns range in millimeters in diameter, whereas microvoltammetry indicator microelectrodes range from single digit microns to a few hundred microns in diameter.

A common misconception is that a microdialysis membrane is a detecting device which, in turn leads, incorrectly, to direct comparisons between microdialysis membranes and microvoltammetry indicator detecting devices. Whether or not microdialysis membranes are the same size as voltammetry microelectrodes is irrelevant because the microdialysis membrane is not the detection technology. Microdialysis membranes simply collect perfusate from brain and this perfusate is then analyzed by HPLC.

Dialysis is a technique based on semipermeability of a collection membrane and is not, itself, a detection technique. Existing methods of detecting glutamate by microdialysis followed by HPLC and electrochemical (EC) detection, actually detect a derivative of glutamate rather than glutamate itself. Similarly, microdialysis methods of detecting the neurotransmitter acetylcholine are based on detecting hydrogen peroxide, not acetylcholine itself (Stoecker P W et al., 1990, Selective Electrode Rev. 12:137–160). Moreover, correlation between the derivative of glutamate or $H_2O_2$ detected and the Cottrell Equation has never been addressed. Therefore, detection of straight chain carbon compounds by the microdialysis membrane method may be questionable. Broderick probes offer an attractive alternative since they may be able to directly detect glutamate or acetylcholine.

Generally, quantitation of neurochemistry is described as a percentage of a few data points, over hours, used as "control" in microdialysis studies. However, Broderick probes are easily calibrated and concentrations are interpolated from calibration curves (Broderick P A et al., 2000, Brain Res. 878:49–63).

One of the advantages of using Broderick probes with microvoltammetry is that microvoltammograms may be obtained from freely moving and behaving living animals and humans. Thus, in some embodiments of the invention another parameter may be monitored and/or recorded. For example, a Broderick probe microvoltammogram may be acquired from a subject while simultaneously monitoring and/or recording the subject's movements (e.g. ambulations and/or fine motor movements). Other examples of parameters that may be monitored and/or recorded include, inter alia, the presence and concentration of a drug, protein, nucleic acid, (e.g. mRNA), carbohydrate, or lipid; consciousness of the subject, cognitive functions, self-administration paradigms, reward-stimulus paradigms, electrophysiological functions, and memory.

The invention provides a variety of methods for identification, diagnosis, and treatment of neuropathologies, neurotoxicities, tumors, and brain and spinal cord injuries using microelectrodes with microvoltammetry. These methods comprise comparing Broderick probe microvoltammograms from at least two different tissues. One these tissues is generally a reference tissue or control. The other is tissue is that being assayed. Preferably, the reference tissue corresponds to the assay tissue with respect to, for example, tissue type, anatomical location, and/or stage of development.

In some embodiments of the invention, the comparison is performed between microvoltammograms taken from the same tissue at different times. In some embodiments, the microvoltammograms compared are taken from the same tissue before and after exposure to a material such as a drug. In some embodiments, a tissue suspected of being diseased is compared with healthy tissue.

Such comparisons may make it possible to diagnose and/or treat a wide variety of diseases or conditions that are associated with abnormal neurotransmitter levels. The invention provides methods comprising exposing at least a cell to a diagnostic challenge or therapeutic treatment, contacting said cell with a Broderick porbe, applying a potential to said Broderick probe; and generating a Broderick probe microvoltammogram. A diagnostic challenge may be designed to elicit a differential response from cells of interest, e.g. diseased cells, from other cells, e.g. healthy cells. A therapeutic treatment may or therapeutic treatment may be known or intended to cure or ameliorate a disease condition. Alternatively, a treatment may be assessed for its capacity to serve as a diagnostic indicator or therapeutic treatment. A diagnostic challenge or a therapeutic treatment may comprise exposing the cell(s) to a material such as a small molecule drug or drug candidate, a defined electrochemical environment (e.g. application of a potential to the cell(s)), exposure to an isotopic or nonisotopic label, activation or repression of a preselected gene, or combinations thereof.

Disorders of basal ganglia, such as athetoid, dystonic diseases, and cancer may be studied with the Broderick probe. An example of an athetoid, dystonic disease is Lesch Nyhan Syndrome (LNS). This recently recognized disease is characterized by severe athetoid and dystonic movements, self-mutilation, and repetitive oral stereotypies. Patients suffering from LNS may have to have their teeth removed to avoid oral stereotypies that cause the patient to devour lips, tongues or fingers. The stereotypies involve DA and 5-HT (Allen SM et al., 1999, Behav. Pharmacol. 10:467–474) and high levels of UA (Patten J, 1980, Neurological Differential Diagnosis, pp. 127–128). Other athetoid and dystonic diseases, such as autism, spinal cord injury, schizophrenia, epilepsy and Parkinson's, are amenable for study with these miniature sensors, even intraoperatively, insofar as epilepsy and Parkinson's are concerned. Several reports indicate that various cancers are also amenable for study with these miniature sensors (Broderick P A, 1989, U.S. Pat. No. 4,883,057; Broderick P A, 1995, U.S. Pat. No. 5,433,710; Broderick P A, 1997, EP 0487647 B1; Broderick P A, 1999, U.S. Pat. No. 5,938,903; Broderick P A, 1999, Hong Kong, HK # 1007350; Broderick P A, 1988, Neurosci. Lett. 95:275–280; Broderick P A, 1989, Brain Res. 495:115–121; Broderick P A, 1990, Electroanalysis 2:241–251; Broderick P A, 2000, Epilepsia 41(Suppl.):91; Broderick P A et al., 2000, Brain Res. 878:49–63).

Much of the difficulty in determining the importance of the alterations in relative concentrations of neurotransmitters and their relationship to epileptogenesis in temporal lobe epilepsy relates to the variability in both the etiology of epilepsy and the location of the epileptogenic zone in epilepsy patients. Few studies have analyzed monoamine concentrations in human epileptic tissue. Those that have studied resected temporal lobe tissue have not distinguished between neocortical temporal lobe epilepsy and mesial temporal lobe epilepsy patients. Neocortical temporal lobe tissue that was part of the ictal onset zone as verified by intracranial EEG recordings of seizures in patients with neocortical temporal lobe epilepsy was examined according to the invention. As previously described (Doyle W K et al., 1997, Epilepsy: A Comprehensive Textbook, pp. 1807–1815), the anterior temporal neocortex in patients with mesial temporal lobe epilepsy is routinely removed at our center to gain access to the mesial temporal structures, providing neocortical tissue controls for our study. While patients with mesial temporal lobe epilepsy may have coexisting neocortical abnormalities like cortical dysplasia (CD), none of the mesial temporal lobe epilepsy patients included in this study had pathologically confirmed CD. Secondary changes such as mild diffuse gliosis were found in the temporal neocortex of mesial temporal lobe epilepsy patients, but we hypothesized that the normal neurochemical profile may still be preserved compared to the actively seizing neocortical tissue analyzed in our neocortical temporal lobe epilepsy patients.

The invention provides devices and methods for diagnosing temporal lobe epilepsy comprising generating a temporally resolved Broderick probe microvoltammogram of a temporal lobe tissue of a subject; and comparing said microvoltammogram to at least one reference Broderick probe microvoltammogram; wherein said reference is a Broderick probe microvoltammogram of the corresponding temporal lobe tissue of another individual. In some embodiments of the invention, the subject's microvoltammogram is compared with one or more reference microvoltammograms from a healthy individual, an individual having mesial temporal lobe epilepsy, an individual having neocortical temporal lobe epilepsy, or combinations thereof.

The invention provides diagnostic devices and methods for brain cancer. In some embodiments the methods comprise: generating a temporally resolved Broderick probe microvoltammetric profile of cancerous cells or tissue; determining from said profile the presence and concentration of at least two markers selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide; and comparing said marker concentrations to specific threshold values of each of the markers to determine the presence of statistically significant concentration differences, preferably $P<0.05$; wherein said threshold values are derived from Broderick probe microvoltammetric profile(s) of healthy cells or tissue and said step of comparing said markers distinguishes whether the cancerous cells are present in gray matter or white matter. In other embodiments, the diagnostic methods comprise generating a temporally resolved Broderick probe microvoltammetric profile of a tissue having or at risk of having a tumor; comparing said microvoltammogram to at least one reference Broderick probe microvoltammogram; wherein said reference is a Broderick probe microvoltammogram of corresponding tissue of a healthy individual, cultured cells thereof, corresponding tissue of a an individual having a tumor, cultured cells thereof, or combinations thereof.

The invention also provides diagnostic devices and methods for brain or spinal cord injury. In some embodiments of the invention these methods comprise: generating a temporally resolved Broderick probe microvoltammogram of a tissue of a mammal having or being at risk of developing a brain or spinal cord injury; simultaneously monitoring movement of said mammal; and comparing said microvoltammogram and movement behavior to a reference microvoltammogram of corresponding tissue of a healthy tissue and reference movement behavior of a healthy individual. In addition, the invention provides methods for detecting a site of nerve damage or blockage. These methods may comprise generating a temporally resolved Broderick probe microvoltammogram of a tissue of said mammal; simultaneously monitoring movement of said mammal; and comparing said microvoltammogram and movement behavior to a reference microvoltammogram of corresponding tissue of a healthy tissue and reference movement behavior of a healthy individual.

The invention provides devices and methods for treating temporal lobe epilepsy comprising generating a temporally resolved Broderick probe microvoltammogram of a temporal lobe tissue of a subject having or at risk of developing a temporal lobe epilepsy; comparing said microvoltammogram to at least one reference Broderick probe microvoltammogram; determining the type and extent of temporal lobe resection necessary to achieve a substantially seizure free outcome; and resecting the subject's temporal lobe accordingly. In some embodiments of the invention, the subject's microvoltammogram is compared with one or more reference microvoltammograms from a healthy individual, an individual having mesial temporal lobe epilepsy, an individual having neocortical temporal lobe epilepsy, or combinations thereof.

Brain or spinal cord injuries as well as nerve damage or blockage treatment may include generating Broderick probe microvoltammograms during therapy, i.e. while a pharmacological therapy or kinesitherapy is being administered. Broderick probe microvoltammograms may be acquired continuously during therapy or at intervals. Likewise, cancer treatments may be adapted to include Broderick probe microvoltammetry during therapy. By generating Broderick probe microvoltammograms, it may be possible to monitor tumor size.

The invention contemplates the use of microvoltammetry to assess the neurotoxicity of any material. In some embodiments of the invention, Broderick probe microvoltammograms are acquired from a neural cell or tissue in the presence and absence of the subject material. Materials that may be tested include controlled substances (e.g. opiates, stimulants, depressants, hallucinogens), anti-depressants, anti-epilepsy drugs, and other psychopharmacological substances.

The term "controlled substances" refers to all substances listed in 21 C.F.R. §1308 even where those referenced only as exceptions. It further includes all salts, geometric and stereoisomers, and derivatives of substances listed therein.

Opiates include, inter alia, alfentanil, alphaprodine, anileridine, apomorphine, bezitramide, carfentanil, cocaine, codeine, 4-cyano-2-dimethylamino-4,4-diphenyl butane, 4-cyano-1-methyl-4-phenylpiperidine pethidine-intermediate-B, dextropropoxyphene, dextrorphan, dihydrocodeine, dihydroetorphine, diphenoxylate, 1-gdiphenylpropane-carboxylic acid pethidine (meperidine), ecgonine, ethyl-4-phenylpiperidine-4-carboxylate pethidine-intermediate-C, ethylmorphine, etorphine hydrochloride, fentanyl, hydrocodone, hydromorphone, isomethadone, levo-alphacetylmethadol, levomethorphan, levorphanol, metazocine, methadone, methadone-intermediate, 2-methyl-3-morpholino-1, 1-methyl-4-phenylpiperidine-4-carboxylic acid, metopon, morphine, moramide-intermediate, nalbuphine, nalmefene, naloxone, naltrexone, opium, oxycodone, oxymorphone, pethidine-intermediate-A, phenanthrene alkaloidsphenazocine, piminodine, racemethorphan, racemorphan, remifentanil, sufentanil, thebaine, and thebaine-derived butorphanol.

Stimulants include substances having a stimulant effect on the central nervous system such as, inter alia, amphetamine, methamphetamine, phenmetrazine, methylphenidate, and salts, isomers, and salts of isomers thereof.

Depressants include substances having a depressant effect on the central nervous system such as, inter alia, amobarbital, glutethimide, pentobarbital, phencyclidine, and secobarbital Hallucinogens include, inter alia, nabilone.

Anti-depression drugs include, inter alia, citalopram, fluvoxamine, paroxetine, fluoxetine, sertraline, amitriptyline, desipramine, nortriptyline, venlafaxine, phenelzine, tranylcypromine, mirtazepine, nefazodone, trazodone, and bupropion.

Anti-epilepsy drugs include, inter alia, carbamazepine, clorazepate, clopazine, ethosuximide, felbamate, gabapentin, lamotrigine, phenobarbital, phenytoin, primidone, topiramate, and valproic acid.

The neurological side effects including neurotoxicity of any pharmaceutical may be assayed according to the methods of the invention. Neurotoxicity of other substances such as minerals, ions, metals (e.g. heavy metals such as mercury and lead), caffeine, ethanol, nicotine, cannabinoids proteins, lipids, nucleic acids, carbohydrates, glycolipids, and lipoproteins may also be assessed using methods of the invention.

EXAMPLES

The following examples illustrate a few embodiments of the invention. Other embodiments will be apparent to one of ordinary skill in the art and do not depart from the scope of the invention.

Example 1

Human Epilepsy

Fourteen patients who had temporal lobectomies for intractable seizures were studied. Patients underwent intraoperative surgery within the same time period and were studied in order of time, within the same time period. Patients were classified as having mesial temporal lobe epilepsy if pathologic examination of the resected temporal lobe revealed severe hippocampal neuronal loss and gliosis and if examination of the neocortex revealed no other etiology for the patient's epilepsy. Nine patients were classified as mesial temporal lobe epilepsy based on these features. Five patients were classified as having neocortical temporal lobe epilepsy based on the lack of hippocampal atrophy on magnetic resonance imaging (MRI) and demonstration of seizure onset in temporal neocortex during chronic intracranial EEG study with lateral temporal subdural grid electrodes and multiple baso-mesial temporal subdural strip electrodes.

FIG. 1 shows a schematic diagram of a Broderick Probe microelectrode. The microelectrode manufacturing process has been published in detail elsewhere (Broderick P A, 1993, Pharmacol. Biochem. Behav. 46:973–984; Broderick P A, 2002, Handbook of Neurotoxicology, Vol. 2, Chapter 13; Broderick P A et al., 2000, Brain Res. 878:48–63). Studies revealed no promotion of bacterial growth on the microelectrodes with and without gamma irradiation (Sterigenics, NC).

The in vivo microvoltammetric measurement was made through the application of a potential (in mV) between the indicator (working) microelectrode and a Ag/AgCl reference microelectrode. Current is formed at the indicator microelectrode that corresponds to the separate electroactive species for dopamine, serotonin, norepinephrine, and ascorbic acid. The resultant electrochemical measurements are called Faradaic because the amount of the oxidative/reductive species detected at the microelectrode surface is calculated by Faraday's Law, which shows that a direct proportionality exists between the charge and the mass of a chemical. The proportionality between charge and mass is described by the Cottrell equation.

Figure 3:
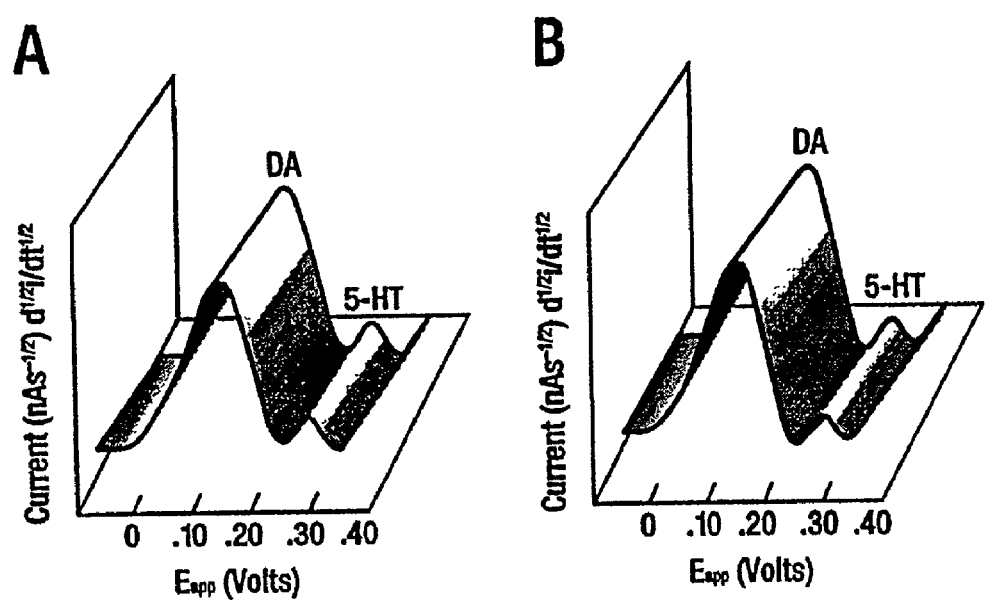
FIG. 3. Microvoltammograms, recorded in vivo in real time of neurons in the nucleus accumbens (NAcc) of freely moving and behaving, male, Sprague-Dawley laboratory rats. The oxidation potential in millivolts is plotted on the x-axis. The current derived from each neurochemical is plotted on the y-axis; Current Scale=25 $pAs^{-1/2}$ 12.5 $mm^{-1/}$ $_2$)]. Panel A was recorded two weeks after surgical implantation of Broderick probes under sodium pentobarbital anesthesia, actually on Nov. 30, 1992 and panel B was recorded seven months later on May 11th, 1993. Both voltammograms represent endogenous release of dopamine (DA) and serotonin (5-HT) in the basal nucleus, NAcc, while the animal is exhibiting normal motor activity in the open-field behavioral paradigm. Animal was not treated with drugs at either recording time, nor was the animal treated with drugs during the seven-month period; recordings taken during the seven-month period were stable as well.

Potentials were applied to the working microelectrode with respect to the Ag/AgCl microelectrode by a CV37 detector-potentiostat, electrically connected to a Minigard Surge Suppressor which is then connected to an isolated electric ground. Each neurotransmitter and neuromodulator was detected within seconds of release at a scan rate of 10mV/s (see FIGS. 3 A&B). In vivo microvoltammetric signatures for neurotransmitters and neuromodulators were determined by experimentally established oxidation potentials. Oxidation potentials were delineated in millivolts. Additionally, lauric acid microelectrodes may be employed for intraoperative recordings due to their extremely rapid equilibration time (Broderick P A et al., 1999, Epilepsia 40(supp17):78–79).

Resected temporal lobe tissue from 14 epilepsy patients was examined in a medium of Ringer's Lactate Buffer solution. Samples were taken from the antero-lateral temporal neocortex. In a faradaic chamber, a reference and an auxiliary electrode were placed in contact with the surface of the specimen and a stearate indicator microelectrode stereotaxically was inserted dorsoventrally, 2 mm into the brain tissue, in situ. With the triple microelectrode assembly in place, potentials were applied and scanned at a rate of 10 mV/sec from an initial voltage of –0.2 V up to a voltage of +0.9 V. The electrochemical signals were recorded on a strip chart recorder.

Figure 4:
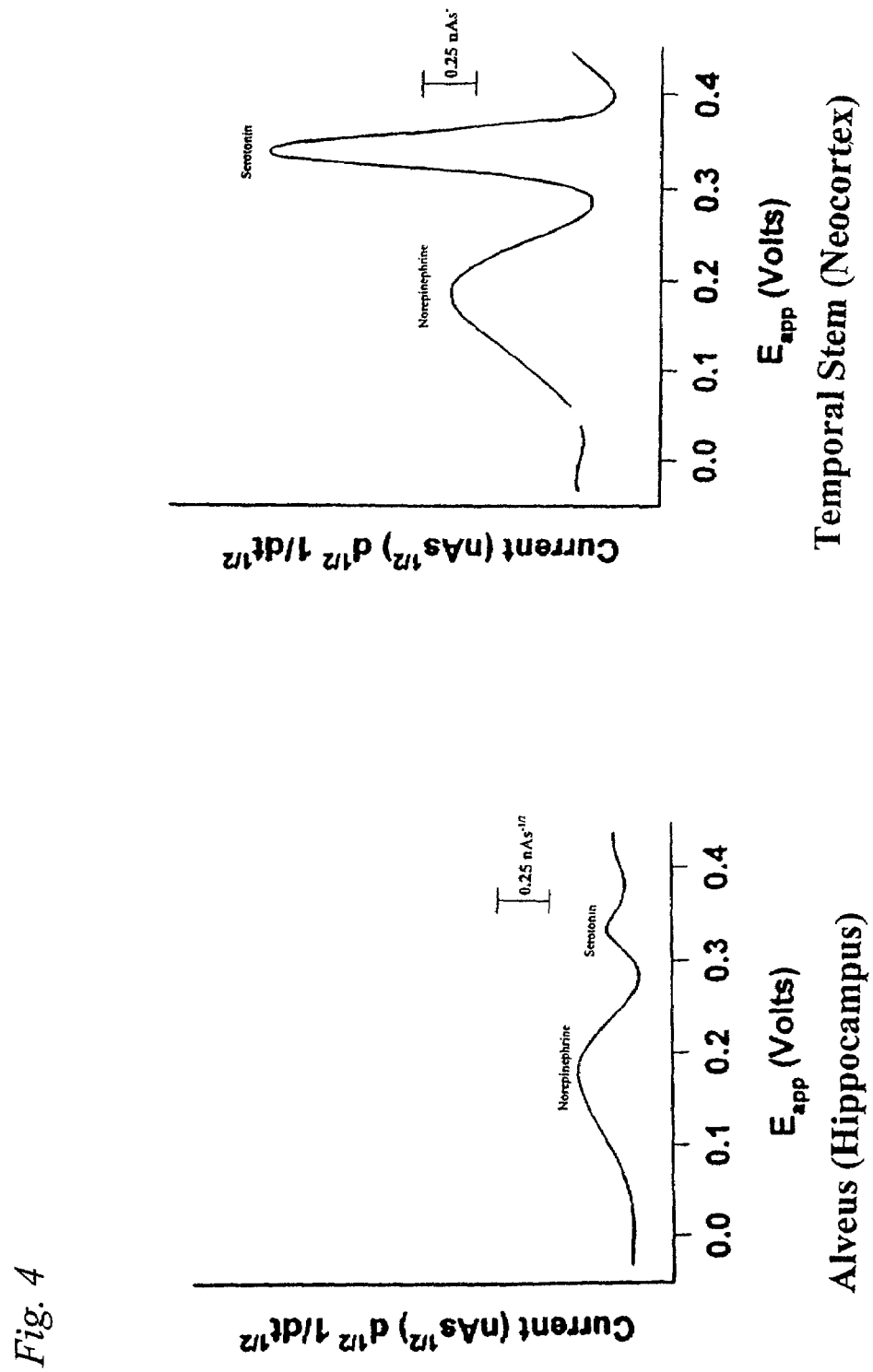
FIG. 4. In situ microvoltammetric recording from hippocampal alveus (white matter in hippocampus, left panel) and neocortex stem (white matter in neocortex, right panel). Tissue was resected from a mesial temporal lobe epilepsy patient (Patient #7).

Table 1 lists the concentrations of norepinephrine, serotonin, and dopamine found in the lateral temporal neocortex (Band of Baillarger) of the nine mesial temporal lobe epilepsy and five neocortical temporal lobe epilepsy patients. Representative Broderick probe voltammograms from patients 8 and 14 are shown in FIG. 4. Four of five neocortical temporal lobe epilepsy patients had no detectable norepinephrine in temporal neocortex while norepinephrine was present in temporal neocortex of eight of nine mesial temporal lobe epilepsy patients (Chi Square, $p<0.01$). The mean norepinephrine concentration was 21.1 nM±5.8 nM. Statistical significance was analyzed by the median according to the Mann-Whitney Rank Sum, ($p<0.065$) for the mesial temporal lobe epilepsy group. In contrast dopamine was detected in the temporal neocortex of three of five neocortical temporal lobe epilepsy patients but in only one of the mesial temporal lobe epilepsy patients (Chi Square, $p<0.05$). The mean dopamine concentration for the neocortical temporal lobe epilepsy group was 16.7 nM±7.6 nM. Individual dopamine concentration for each neocortical temporal lobe epilepsy patient was compared with dopamine concentration from each mesial temporal lobe epilepsy patient. Dopamine was significantly greater in neocortical temporal lobe epilepsy vs. mesial temporal lobe epilepsy (Mann-Whitney Rank Sum, $p<0.027$).

TABLE 1

Monoamine Concentrations in the Neocortex (Band of Baillarger) in MTLE and NTLE Patients.

| Patient # | MTLE | | Patient # | NTLE | |
|---|---|---|---|---|---|
| 1 | NE 48.3 | 5-HT 1.5 | 10 | DA 17.8 | 5-HT 2.0 |
| 2 | NE 8.6 | 5-HT 1.7 | 11 | DA 29.2 | 5-HT 2.1 |
| 3 | NE 5.6 | 5-HT 1.3 | 12 | AA 0.11 | 5-HT 4.9 |
| 4 | NE 4.3 | 5-HT 1.3 | 13 | NE 44.8 | 5-HT 1.7 |
| 5 | NE 17.2 | 5-HT 1.9 | 14 | DA 3.0 | 5-HT 2.2 |
| 6 | DA 17.2 | 5-HT 2.0 | | | |
| 7 | NE 25.8 | 5-HT 3.5 | | | |

TABLE 1-continued

Monoamine Concentrations in the Neocortex (Band of Baillarger) in MTLE and NTLE Patients.

| Patient # | MTLE | | Patient # | NTLE | |
|---|---|---|---|---|---|
| 8 | NE | 5-HT | | | |
| | 8.5 | 3.2 | | | |
| 9 | NE | 5-HT | | | |
| | 11.6 | 3.6 | | | |

Pathology for patients 1 through 9 is hippocampal disease; pathology for patients 10 through 14 is neocortical disease. Values for monoamines [Norepinephrine (NE), Serotonin (5-HT), Dopamine (DA)] are calibrated in nM concentrations. Values for Ascorbic Acid (AA) were calibrated in μM concentrations. Neurochemical signatures for mesial temporal lobe epilepsy patients consisted of the presence of norepinephrine and 5HT and the absence of dopamine in each neocortical specimen with the exception of patient #6, who exhibited dopamine and not norepinephrine. Neurochemical signatures for neocortical temporal lobe epilepsy patients consisted of the presence of dopamine, serotonin and ascorbic acid and the absence of norepinephrine in each neocortical specimen with the exception of patient, #14 who exhibited norepinephrine and not dopamine.

Serotonin was detected in the temporal neocortex of all 14 patients, with a mean concentration of 2.2 nM ±0.32 for the mesial temporal lobe epilepsy patients and 2.58 nM ±0.59 for the neocortical temporal lobe epilepsy group. Ascorbic acid was found in the temporal neocortex of one of the neocortical temporal lobe epilepsy patients at a concentration of 0.1 μM, but in none of the mesial temporal lobe epilepsy patients.

The most striking finding of this study was the marked norepinephrine depletion seen in the temporal neocortex of neocortical temporal lobe epilepsy patients compared with that of the mesial temporal lobe epilepsy patients. In experimental models, norepinephrine may differentially enhance or inhibit GABAergic cells (Kawaguchi Y et al., 1998, J Neurosci 18:6963–6976). However, in numerous experimental models of epilepsy, norepinephrine depletion has been shown to enhance the frequency, intensity, and spread of seizures (Browning R A et al., 1989, J Pharmacol Exp Ther 249:229–35; Ferrendelli J A et al., 1986, Adv. Neurol. 44:393–400). A consistent depletion in neocortical norepinephrine has not been previously demonstrated in human epilepsy. One study by Goldstein et al. (Goldstein D S et al., 1988, J Neurochem 50:225229), using intraoperative electrocorticography, showed increased concentrations of norepinephrine in spiking cortex compared with nonspiking cortex. This increased concentration was hypothesized to be a compensatory, inhibitory role of norepinephrine. However, this study used whole tissue homogenates of large cortical regions and it is difficult to compare these data to the restricted neocortical samples examined in this Example. Subtypes of temporal lobe epilepsy were also not considered. In another study of 20 patients with TLE by Pintor and colleagues, no difference in norepinephrine concentrations were found between spiking and nonspiking regions (Pintor M et al., 1990, Synapse 5:152–156).

These results suggest that the Band of Baillarger is white matter.

TABLE 2

Statistical Results.

| | |
|---|---|
| 1) Results showed that the neurotransmitter DA in temporal neocortex of NTLE patients was significantly greater that in MTLE patients: Chi-square - p < 0.05 for presence vs. absence of DA; Mann-Whitney Rank Sum - p = 0.027 (p < 0.01) for concentration of DA in NTLE to be significantly greater than that of MTLE | DA NTLE > MTLE |
| 2) 5-HT: Chi-square (not applicable); Mann-Whitney Rank Sum - p = 0.317. Not Significant (N.S.) | 5-HT N.S. |
| 3) NE concentrations in temporal neocortex were significantly greater in MTLE than in NTLE patients: Chi-square - p < 0.01; Mann-Whitney Rank Sum - p = 0.065 (p < 0.01) | NE MTLE > NTLE |
| 4) AA: Chi-square - p < 0.2; Mann-Whitney Rank Sum - p = 0.894. | AA NTLE > MTLE trend: Chi square |

The most striking finding of this study was the marked norepinephrine depletion seen in the temporal neocortex of our neocortical temporal lobe epilepsy patients compared with that of the mesial temporal lobe epilepsy patients. In experimental models, norepinephrine may differentially enhance or inhibit GABAergic cells (Kawaguchi Y et al., 1998, J Neurosci 18:6963–6976). However, in numerous experimental models of epilepsy, norepinephrine depletion has been shown to enhance the frequency, intensity and spread of seizures (Browning R A et al., 1989, J Pharmacol Exp Ther 249:229–35; Ferrendelli J A et al., 1986, Adv. Neurol. 44:393–400). To our knowledge, a consistent depletion in neocortical norepinephrine has not been previously demonstrated in human epilepsy. One study by Goldstein et al. (Goldstein D S et al., 1988, J Neurochem 50:225229), using intraoperative electrocorticography, showed increased concentrations of norepinephrine in spiking cortex compared with nonspiking cortex. This increased concentration was hypothesized to be a compensatory, inhibitory role of norepinephrine. However, this study used whole tissue homogenates of large cortical regions and it is difficult to compare these data to the restricted neocortical samples in our study. Subtypes of temporal lobe epilepsy were also not considered. In another study of 20 patients with TLE by Pintor and colleagues, no difference in norepinephrine concentrations were found between spiking and nonspiking regions (Pintor M et al., 1990, Synapse 5:152–156).

Example 2

Human Epilepsy

Significant differences in the monoamine signatures from the hippocampal subparcellations in patients with MTLE and NTLE have been observed. The alveus (hippocampal white matter) contains both efferent fibers from hippocampus that form the fornix and afferent pathways connecting entorhinal cortex and the CA1 region of the hippocampus. The neurochemistry of the alveus in patients with MTLE and NTLE was studied to determine whether similar neurotransmitter alterations exist.

Microvoltammetry with Broderick probe stearic acid microelectrodes was used to detect norepinephrine (NE), dopamine (DA), ascorbic acid (AA), and serotonin (5-HT) in resected temporal lobes of 9 MTLE and 4 NTLE patients with temporal lobe epilepsy. Neurotransmitters were detected in separate signals within the same recording within seconds in alveus by experimentally derived oxidative potentials, determined in vitro in Ringers Lactate or $PO_4$ buffer. Ag/AgCl reference and stainless steel auxiliary micro electrodes were placed in each specimen 4–6 mm from indicator microelectrodes (patented)(manufactured on site). Methods are published (Broderick P A, 1989, Brain Res. 495:115–121; Broderick P A, 1988, Neurosci. Lett. 95:275–280; Broderick P A et al., 2000, Brain Res. 878: 48–63; Pacia SV, 2001, Brain Res. 899(1–2):106–11). All signals were analyzed for the presence of diffusion peaks in early oxidative species (indicating white matter).

All of the NTLE patients had significant DA in the alveus while only one MTLE patient had detectable DA ($p<0.01$, Mann-Whitney Rank Sum Test). Eight of the nine MTLE patients had significant NE in alveus while none of the concentrations were significantly higher in NTLE specimens ($p<0.01$, Mann-Whitney Rank Sum Test).

The neurochemical profiles in alveus of patients with MTLE and NTLE reveal neurotransmitter alterations similar to those alterations seen in the hippocampal pyramidal cell layer of these patients, a region with direct afferent and efferent connections through the alveus.

Example 3

Distinguishing White and Gray Matter

Voltammetric signals were analyzed from microelectrodes in resected temporal lobes to determine whether gray and white matter structures could be reliably distinguished.

Microvoltammetry with Broderick Probe stearic acid microelectrodes was used to detect norepinephrine (NE), dopamine (DA), ascorbic acid (AA), and serotonin (5-HT) in 40 grey matter structures and 37 white matter structures in resected temporal lobes of a total of 14 patients with temporal lobe epilepsy. Neurotransmitters were detected in separate signals within the same recording within seconds in 3 gray matter (temporal neocortex, hippocampal pyramidal, and dentate gyrus granular layer) and 3 white matter structures (temporal stem, subiculum, and alveus), by experimentally derived oxidative potentials, determined in vitro in Ringers Lactate or $PO_4$ buffer. Ag/AgCl reference and stainless steel auxiliary microelectrodes were placed in each specimen 4–6 mm from indicator microelectrodes (patented) (manufactured on site). Methods are published (Broderick P A, 1989, Brain Res. 495:115–121; Broderick P A, 1988, Neurosci. Lett. 95:275–280; Broderick P A et al., 2000, Brain Res. 878:48–63; Pacia S V, 2001, Brain Res. 899 (1–2):106–11). All signals were analyzed for the presence of diffusion peaks in early oxidative species (indicating white matter).

Figures 5A, 5B:
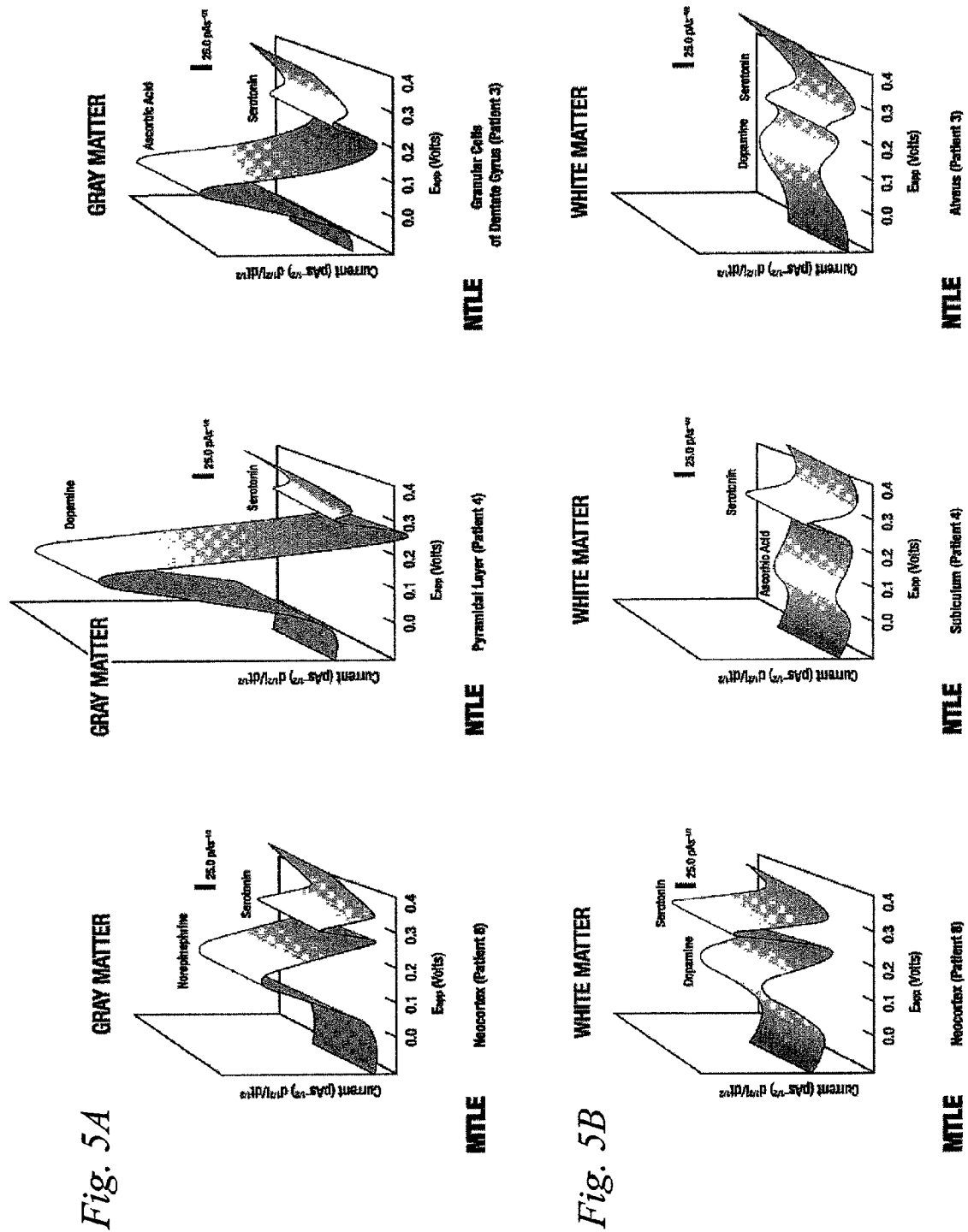
FIG. 5. (A) Gray Matter recordings (Voltammograms) from resected tissue from temporal lobe epilepsy patients. Left to Right: Neocortex, Patient 8; Pyramidal Layer, Patient 4; Granular Cells of the Dentate Gyrus, Patient 3. (B) White Matter recordings (Voltammograms) from resected tissue from temporal lobe epilepsy patients. Left to Right: Neocortex, Patient 8; Subiculum, Patient 4; Alveus, Patient 3. X-axis: Oxidation potentials in millivolts. Y-axis: Current in picoamperes per semidifferentiation of the second.
Figure 6:
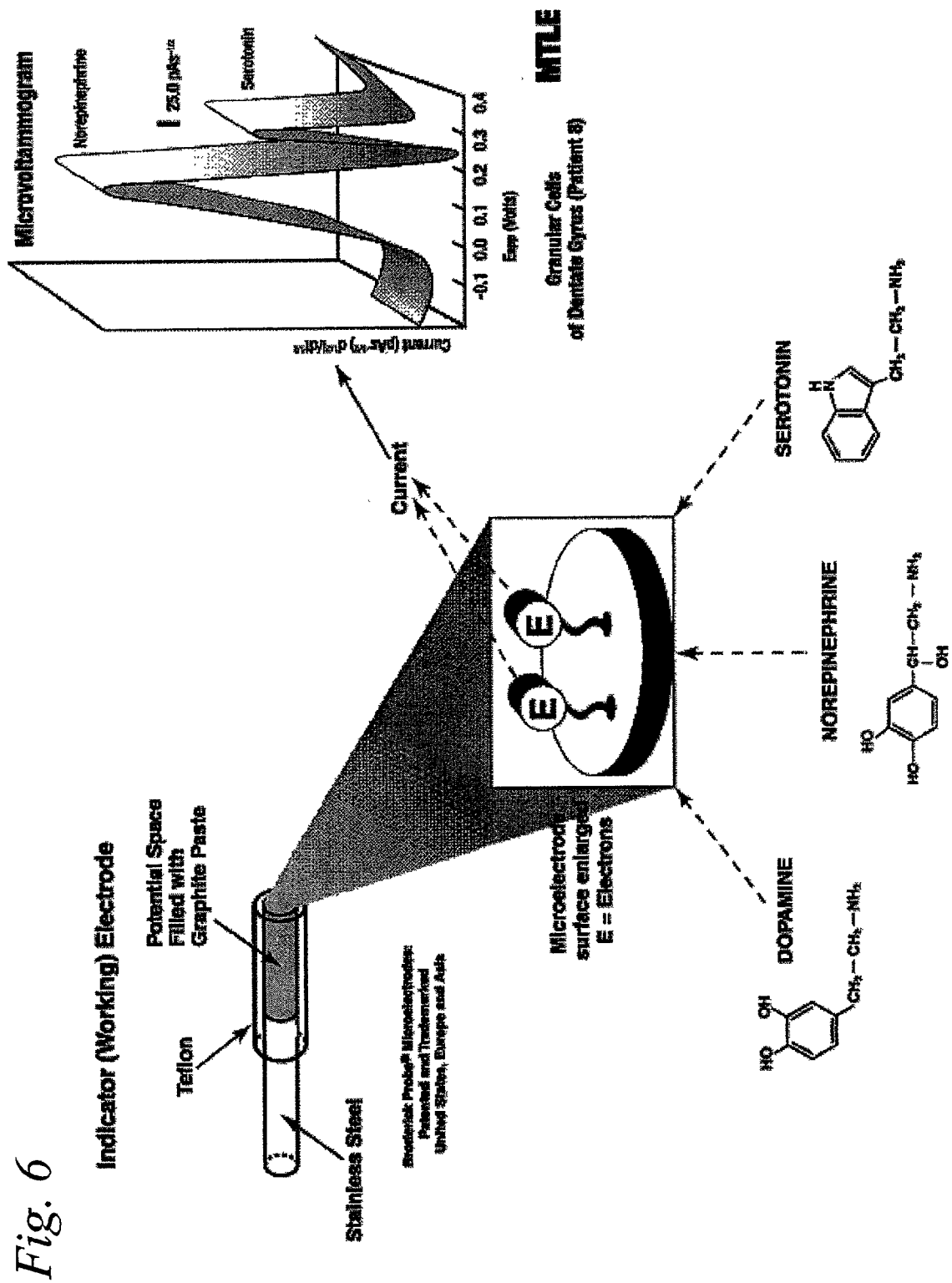
FIG. 6. Illustration of Broderick probe operation detecting neurotransmitters along with a resulting microvoltammogram.

FIG. 5 shows representative examples of distinctive signals recorded from grey matter (A) and white matter (B). Criteria for distinguishing electrochemical signals for gray versus white matter consist of distinct differences in the catecholamine (i.e. dopamine, norepinephrine) peaks, peaks that are called the "early oxidative species". They are as follows:

(A) Gray matter signals are large in amplitude denoting high concentrations, whereas white matter signals are small in amplitude denoting low concentrations of neurotransmitters. Moreover, white matter signals are defined electrochemically as "broad diffusion waveforms".

Criteria for denoting distinct differences in the indoleamine peaks, e.g. serotonin, peaks that are exhibited later than the catecholamines in the oxidative sweep pathway, consist of the following:

(B) Gray matter signals for serotonin are generally lower than those in white matter. White matter signals exhibit a sharp adsorptive waveform.

Of 40 temporal lobe gray matter structures sampled, 39 displayed signals consistent with grey matter and only 1 revealed signals consistent with white matter. Of 37 white matter structures sampled, 30 exhibited signals consistent with white matter. Additionally, white matter tended to have substantially lower concentrations of catecholamines and 5-HT as well as lower ratios of catecholamines to 5-HT. In some prefered embodiments of the invention, the first peak, i.e. catecholamine, for white matter is about two-fold less than the same peak for white matter. In some prefered embodiments, the second peak, i.e. serotonin, for white matter is about two-fold more than the same peak for white matter.

Gray matter has an inherent neuroanatomic difference from white matter and this difference may explain specific waveforms for gray matter versus white matter signals. In gray matter, calcium ions course into fibers through calcium channels which gate neurotransmitters. Calcium channels are absent in white matter and gating of neurotransmitters occurs through sodium channels. In situ microvoltammetry with microelectrodes reliably distinguishes temporal lobe gray matter from white matter, both in the neocortex and in other neuroanatomic substrates such as specific hippocampal parcellations that are comprised of white matter versus gray matter. These results have important implications for in vivo and/or intraoperative neurochemical analysis of human epilepsy. These findings should enable more precise intraoperative neuroanatomic localization.

Furthermore, these findings have important implications for distinguishing and locating tumors/neoplasms and the like, intraoperatively and otherwise especially when these tumors whether they be associated with epilepsy or not, infiltrate other tissues. To date, magnetic resonance imaging (MRI) is unable to detect tumors infiltrated to other tissues.

Example 4

Distinguishing White and Gray Matter

This example is directed to elucidating significant differences in the levels of catecholamine neurotransmitters, dopamine (DA), norepinephrine (NE) and indoleamine neurotransmitter, serotonin (5-HT) in the alveus and temporal stem of 14 intractable epileptic patients, including 9 Mesial Temporal Lobe Epilepsy (MTLE) and 5 Neocortical (lateral) Temporal Lobe Epilepsy (NTLE) patients who underwent surgery. DA, NE, and 5-HT were detected separately according to their experimentally established oxidative potentials. This detection was achieved with in vivo electrochemistry, which depended on a semi-differential microvoltammetry-based system of microelectrodes, consisting of a miniature carbon sensor (Broderick probe®), Ag/AgCl reference microelectrode, and auxiliary micro electrode. Methods are published by Broderick (Broderick P A, 1989, Brain Res. 495:115–121; Broderick P A, 1988, Neurosci. Lett. 95:275–280). Relative to NTLE specimens, MTLE specimens exhibited a reduced level of DA and higher level of NE in alveus and temporal stem. Although, 5-HT was common to all specimens, NTLE specimens showed a significantly higher level in the alveus. The data indicate that MTLE and NTLE are characterized by distinct neuronal microenvironment and that epilepsy-associated gliosis could affect extraneuronal monoamine.

Classically, glial cells have been considered to comprise a passive framework that supports, nourishes, and insulates neurons. They have not been thought of as active factors in the onset and progression of brain disease such as epilepsy. Epilepsy is frequently defined as a neuronal disease marked by spontaneous recurring seizures accompanied by significant biochemical imbalances. Recent studies show that glial cells—the major component of alveus and temporal stem—are actively involved in regulating extraneuronal ions (Bordey A et al., 1998, Epilepsy Res. 32:286–303; Walz W, 1989, Prog. Neurobiol. 33: 309–333) neurotransmitters (Kimelberg H K et al., 1993, Astrocytes, Pharmacology and Function, pp. 193–228) that are involved in the propagation of epilepsy. Electron microscopic sections also show that astrocytes encapsulate neuronal cell bodies and reach closely into the vicinity of synapses. Such anatomical intimacy gives astrocytes access to regulate the neuronal microenvironment.

Numerous studies clearly indicate the relevance of monoamines and their regulation by glial cells towards the propagation of epilepsy. The instant example illustrates how microelectrodes may be used to delineate the levels of catecholamines and serotonin in the hippocampal and neocortical white layers of epileptic tissue. Specifically, the system of microelectrodes utilized herein made it possible to delineate the levels of DA, NE, and 5-HT in the alveus and temporal stem. Consequently, it was possible to assess the impact of epileptic seizure and its consequences on the regulation of extraneuronal catecholamines and serotonin in MTLE and NTLE tissues by comparing neurotransmitter levels before and during a seizure.

Hippocampal and temporal cortex resected from fourteen intractable epilepsy patients was immersed in Ringer's Lactate Buffer Solution. A miniature carbon sensor (Broderick probe) was inserted dorsoventrally (1 mm or 2 mm) into alveus and temporal stem, while a Ag/AgCl reference and auxiliary microelectrodes were placed in contact with the surface of the specimen. This system of microelectrodes has been proven capable of detecting catecholamine DA, NE and indolamine 5-HT neurotransmitters and their metabolites. Methods are published (Broderick P A, 1989, Brain Res. 495:115–121; Broderick P A, 1988, Neurosci. Lett. 95:275–280). Potentials were applied and scanned at a rate of 10 mV/sec from –0.2V to +0.9V across the reference and indicator microelectrodes via a CV-37 Electrochemical Detector (BAS, West Lafayette, Ind.). Each of the 4 monoamines was detected separately at its characteristic oxidative potential, which was experimentally determined (Broderick P A, 1989, Brain Res. 495:115–121; Broderick P A, 1988, Neurosci. Lett. 95:275–280). The resulting electrochemical signals were recorded on a Fisher Recordall® Series 5000 (Houston instruments, Houston, Tex.). The data were statistically analyzed using Chi-square Test, and Mann Whitney Rank Sum Test.

In the alveus, there was a significant decrease in the concentrations of DA in MTLE specimens relative to NTLE specimens (p=0.011; Mann-Whitney Rank Sum Test), and a significant presence of NE in NTLE specimens relative to MTLE (p<0.01; Chi-square). There was a significant depletion in the concentration of NE in NTLE alveus specimens relative to MTLE (p=0.031; Mann-Whitney Rank Sum Test), and a significant occurrence of NE in MTLE relative to MTLE specimens (p<0.001; Chi-square). Although the concentrations of 5-HT are significantly higher in NTLE alveus specimens (p=0.045; Mann-Whitney Rank Sum Test). The actual recording for Patient #7 is shown in FIG. 4A. Patient #7 was diagnosed as having mesial temporal lobe epilepsy.

There was depletion of NE in the NTLE temporal stem specimens relative to MTLE temporal stem specimen [p=0.082]. Chi-square test showed a significant presence of NE in MTLE relative to NTLE specimens (p<0.05). There was no statistical difference in the concentration and occurrence of 5-HT in temporal stem (white matter) MTLE and NTLE specimens. The actual recording for Patient #7 is shown in FIG. 4B.

The results indicate a notable dysfunction in the extraneuronal regulation of (a) DA, NE, and 5-HT in the alveus of MTLE and NTLE patients, and (b) DA and NE in temporal stem of NTLE versus MTLE. These extraneuronal trends extend previous findings that "subtypes of epilepsy are associated with distinct neuronal biochemistry in human neocortex and hippocampus of MTLE and NTLE patients" (Broderick P A et al., 2000, Brain Res. 878:48–63). These differences are extended to white matter hippocampal subparcellations such as alveus and neocortical white matter such as temporal stem.

The significant depletion of DA in the alveus of MTLE specimens may be interpreted as (i) the outcome of increased compensatory DA metabolism in the neuronal microenvironment either by dopamine-β-hydroxylase to NE; or possibly by monoamine oxidase to DOPAC; or still by tryosinase, prostaglandin H synthase and/or xanthine oxidase to the toxic DA quinone; (ii) indication of dopaminergic neuronal death, an evidence of the cytotoxic effect of DA quinone. This explanation conforms with the model of cytotoxic and genotoxic potential of DA via DA quinone, as advanced by (Stokes A H et al., 1999, J. Neurosci. Res. 55:659–665).

Microelectrodes with microvoltammetry as described in the present invention may be utilized to study movement disorders whether they originate in the brain or the spinal cord. This is because this is the first technology that can detect neurotransmitters at the same time that movement occurs. Thus, for spinal cord injury, e.g., Broderick probes are implanted or inserted into neurons and/or interneurons of muscle and ganglia either in situ or in vivo, dysfunction between neurotransmitter and movement is directly detected for appropriate therapeutic interventions. The following examples show how normal behavior, which is rhythmic, needs to be rhythmic with the neurotransmitter, serotonin for normal functioning of brain and spinal cord. This example has been described previously in this application. When injury occurs, irregular synchrony between neurotransmitter and movement is seen with this technology. This is shown by using cocaine also in FIGS. 7–11.

Example 5

Figure 7:
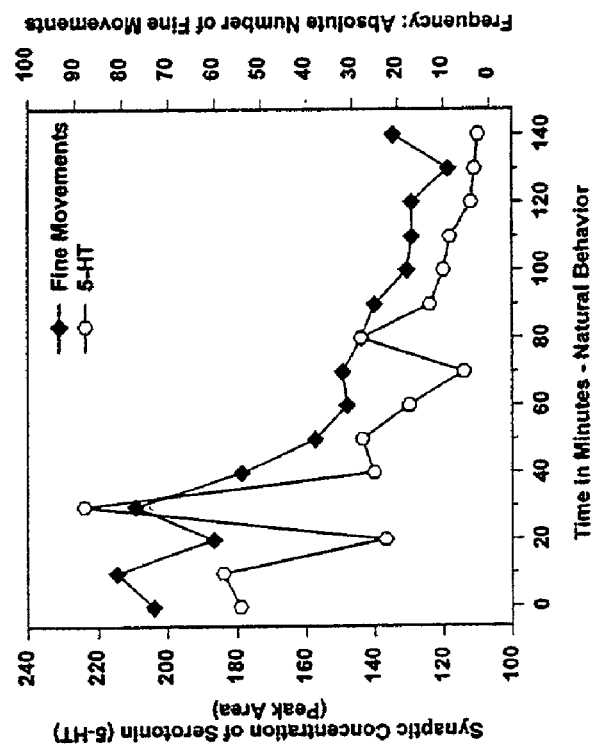
FIG. 7. Neurochemistry and Behavior: Line graph depicting endogenous 5-HT release (open circles) at basal nucleus, Ag terminals, of neurons in the dorsal striatum (DStr), detected in real time, while the freely moving, male, Sprague-Dawley laboratory rat is actually behaving, during normal/natural movement (first hour) and subsequent habituation behavior (second hour). Serotonin, detected within seconds of release, is plotted with a line graph derived from infrared photobeam monitoring of behavior (closed circles): locomotion (ambulations, left panel); stereotypy (fine movements, right panel). Open-field behaviors were studied in units of frequency of events recorded every 100 ms during normal/natural behavior. Data show that normal episodic, rhythmic nature of locomotor movement may be neuromodulated by 5-HT within the basal nucleus.
Figure 7:
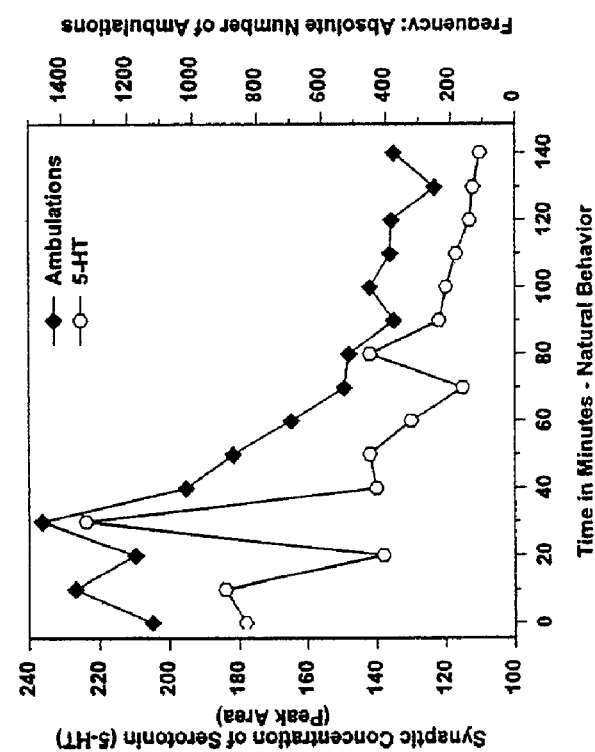

Serotonin Within Motor Circuits Modulates Rhythmic, Episodic Movement During Normal Behavior In FIG. 7, release of 5-HT within DStr, an $A_{9\ D4}$ basal nucleus and nerve terminal field is plotted with ambulations (left panel) and fine movements (right panel). Ambulations are locomotion-movement in the horizontal plane, around the inside of the behavioral chamber; also called open-field behavior or locomotor activity. These may be monitored by computerized infrared photocell beams, located around the outside of the behavioral chamber. Fine movements are called stereotypic movements and consist of repetitious movements and/or rhythmic movements, e.g. rearing, chewing, sniffing. and grooming.

These studies were performed in real time during open-field locomotor (exploratory) and stereotypic behaviors from time 0 min to time 60 min as movement occurred. Serotonin release in this motor nucleus is rhythmic with movement even as movement waxed and waned. This was an intriguing and exciting result since locomotion is known to be not only rhythmic but, very importantly, it is known to be episodic, unlike most other rhythmic and repetitive behaviors.

Figure 8:
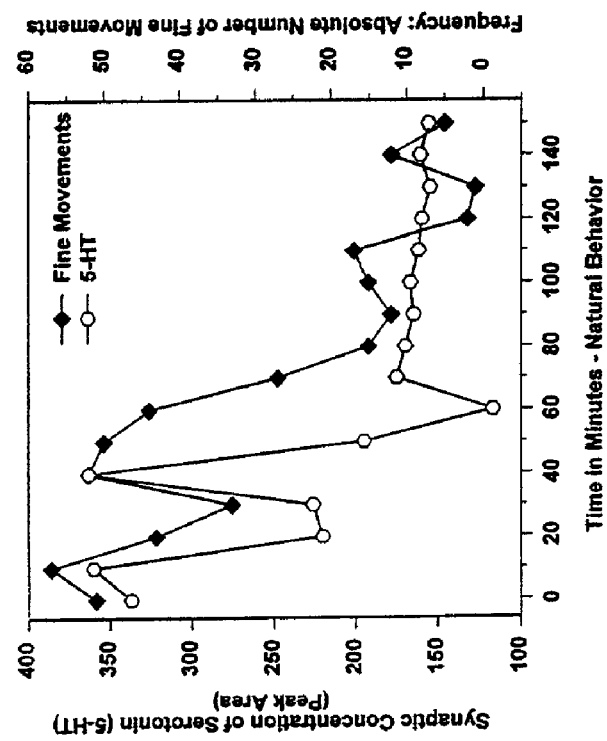
FIG. 8. Neurochemistry and Behavior: Line graph depicting endogenous 5-HT release (open circles) at basal nucleus $A_{10}$ terminals, ventrolateral nucleus accumbens (vlNAcc), in real time, while the freely moving, male, Sprague-Dawley laboratory rat is actually behaving, during normal/natural movement (first hour) and subsequent habituation behavior (second hour). Serotonin, detected within seconds of release, is plotted with a line graph derived from simultaneous infrared photobeam monitoring of behavior (closed circles): locomotions (ambulations, left panel); stereotypy (fine movements, right panel). Open-field behaviors were studied in units of frequency of events, which were recorded every 100 ms during normal/natural locomotor behavior. Data show that normal episodic, rhythmic nature of locomotor movement may be neuromodulated by 5-HT within the basal nucleus, $A_{10}$ terminals.
Figure 8:
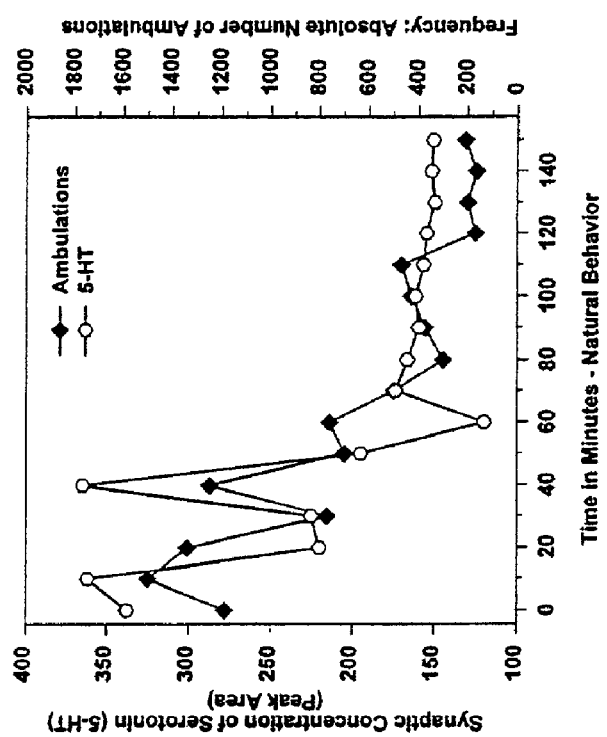

In FIG. 8, release of 5-HT within NAcc core, an $A_{10}$ DA basal nucleus and nerve terminal field is plotted with ambulations (left panel) and fine movements (right panel). NAcc core is a motor nucleus, as is DStr. These studies, also performed in real time, show that 5-HT was released in a motor nucleus, again, rhythmically and episodically during the open-field paradigm study of locomotor (exploratory) and stereotypic behaviors as movement occurred, and again, even as movement's episodic nature was clear. Both FIGS. 7 and 8 show that 5-HT release was rhythmic with both movement and cessation of movement over the habituation period that was initiated and continued from time 60 min to time 120 min. Although the frequency of ambulations and fine movements was not significantly different between studies shown in FIGS. 7 and 8, the extent of 5-HT released in $A_9$ was dramatically less than that released in $A_{10}$ basal nucleus.

The data show a correlation between the 5-HT released within basal nuclei and the motor performance of the animal in the open-field paradigm. Moreover, the rhythm between 5-HT released within $A_9$ basal nucleus and motor behavior is remarkably similar to that rhythm seen between 5-HT released within $A_{10}$ basal nucleus and motor behavior. Similar results were expected from these $A_9$ and $A_{10}$ core because the Broderick probe indicator microelectrode was implanted in NAcc core, the motor-related area of NAcc.

Thus, 5-HT within terminal basal nuclei affects rhythmic movement during the normal/natural operation of repetitive motor behaviors. Serotonin release within the $A_9$ terminal field, DStr, and the $A_{10}$ terminal field, v1NAcc, increased as each open field behavior increased. The 5-HT is released within basal nuclei in synchrony with the changes in motor behavior controlled by the same nuclei.

Lucki, in a 1998 review, states, "diminished 5-HT causes increased exploratory or locomotor activity" (Lucki I, 1998, Biol. Psychiat. 44:151–162). But, there are considerable data that show that 5-HT increases as exploratory or locomotor movement increases. See e.g., Bouhuys A L et al., 1977, Physiol. Behav. 19:535–541; Kohler C et al., 1978, Pharmacol. Biochem. Behav. 8:223–233; Lorens S A et al., 1976, Brain Res. 108:97–113; Schlosberg A J et al., 1979, J. Pharmacol. Exp. Therap. 211:296–304; Srebro B et al., 1975, Brain Res. 89:303–325; Hillegaart V et al., 1989, Pharmacol. Biochem. Behav. 32:797–800; Yeghiayan S K et al., 1997, Pharmacol. Biochem. Behav. 56:251–259. The technology provided here enables scientists to move away from gross behavioral studies which simply average events over long periods of time and space.

Figure 9:
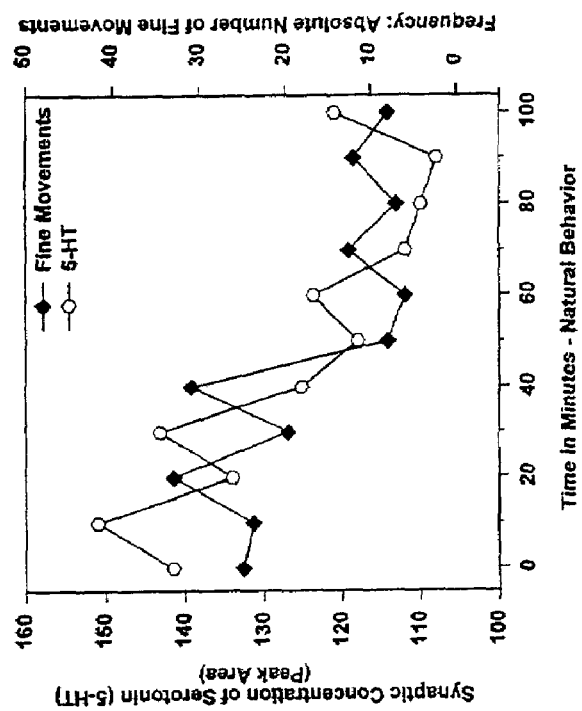
FIG. 9. Neurochemistry and Behavior: Line graph depicting endogenous 5-HT release (open circles) at basal stem nucleus, DA A10 terminals, somatodendrites, ventral tegmental area (VTA), in real time, while the freely moving, male, Sprague-Dawley laboratory rat is actually behaving, during normal/natural movement (first hour) and subsequent habituation behavior (second hour). Serotonin, detected within seconds of release, is plotted with a line graph derived from simultaneous infrared photobeam monitoring of behavior (closed circles): locomotion (ambulations, left panel); stereotypy (fine movements, right panel). Open-field behaviors were studied in units of frequency of events, which were recorded every 100 ms during normal/natural locomotor behavior. Data show that normal episodic, rhythmic nature of locomotor movement is exhibited and can be detected with this biotechnology. However, still, very rhythmic, 5-HT neuromodulation of movement in VTA exhibits a different pattern of rhythm with movement than that pattern, seen in basal nuclei.
Figure 9:
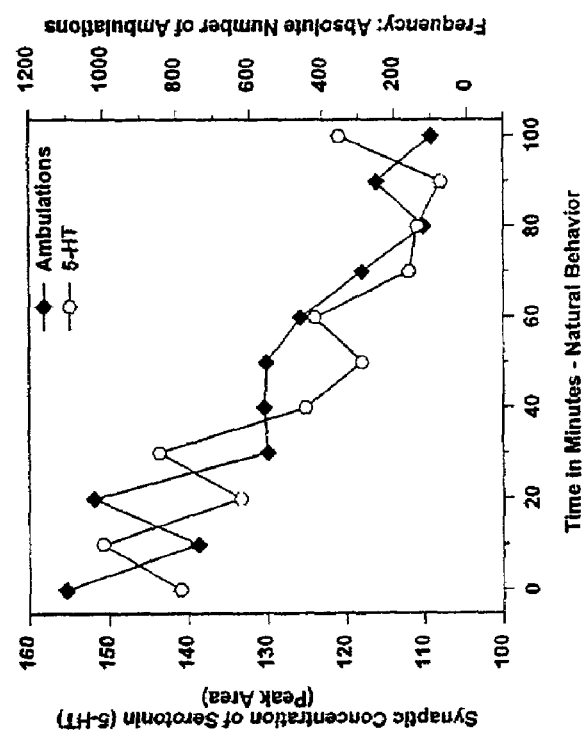

In FIG. 9, 5-HT release within $A_{10}$ somatodendrites is plotted with ambulations (left panel) and fine movements (right panel). These data show that 5-HT was released in a motor brain stem nucleus rhythmically and episodically during the usual, normal/natural operation of movement behaviors. Habituation brought about a decrease in 5-HT release as well as a decrease in locomotor and stereotypic behaviors. Serotonin release in VTA was less than that seen in the basal nuclei.

Within DA somatodendrites, release of 5-HT dramatically increased in a synchronous and rhythmic manner with ambulations and fine movement behaviors of grooming and sniffing. Yet, the temporal relationship between 5-HT released within $A_{10}$ somatodendrites, VTA, with movement is different from that 5-HT released in $A_{10}$ terminals and in As terminals, with movement. Still highly rhythmic, 5-HT release within $A_{10}$ somatodendrites affects movement in a juxtaposed pattern that was not seen in basal nuclei DA nerve terminals, $A_9$ DStr or within $A_{10}$ NAcc core. This was also an intriguing and exciting result since $A_{10}$ somatodendrites are not basal nuclei; $A_{10}$ cell bodies is a brain stem nucleus, comprised of DA somatodendritic neurons projecting to $A_{10}$ basal nuclei.

Increased somatodendritic 5-HT cell firing within 5-HT somatodendrites which occurs before movement behavior occurs (Jacobs B L et al., 1991, Pharmacol. Rev. 43:563–578) and influences DA interactions within terminal basal nuclei (Broderick P A et al., 1997, Neuroscience and Biobehavioral Reviews 21(3):227–260) may be an important mechanism managing the communication between 5-HT released within DA somatodendrites during concurrent open-field ambulatory and fine movement behavior. Also, the dendritic release of DA somatodendritic autoreceptors on DA cells (Grace A et al., 1985, Neurotransmitter Actions in the Vertebrate Nervous System, Chapter 9) with calcium conductance properties, typical of cells exhibiting dendritic release of neurotransmitter (Llinas R et al., 1984, Brain Res. 294:127–132), may be an important component of DA neuronal responsiveness. The short time lag could be due to suppressed DA somatodendritic excitability influenced by dorsal raphe (DR) stimulation (Trent F et al., 1991, Exp. Brain Res. 84:620–630).

From FIGS. 7 through 9, a synopsis of important messages about normal/natural 5-HT release within two basal nuclei, a brain stem nucleus and movement behaviors follows.

5-HT released within $A_9$ and $A_{10}$ core basal nuclei and $A_{10}$ somatodendrites, increased with locomotor behavior and with the fine movement stereotypic behaviors of grooming and sniffing; 5-HT decreased during habituation when movement had essentially ceased.

5-HT release within $A_9$ and $A_{10}$ (core) basal nuclei exhibits rhythmicity in synchrony with locomotion and stereotypic behavior; dramatically similar rhythmic patterns occurred within both basal nuclei.

5-HT released within $A_{10}$ somatodendrites, DA cell bodies, VTA, also showed remarkable rhythmicity with movement and stereotypic behavior, but the rhythmic control by 5-HT in $A_{10}$ somatodendrites assumes a different pattern that that pattern observed when basal nuclei were studied. VTA is brain stem nucleus and not a basal nucleus.

Data demonstrate normal/natural rhythmic episodic movement behaviors, which previous technologies did not enable.

5-HT release within $A_{10}$ (core) DA nerve terminals during movement and stereotypic behaviors was greater than within $A_9$ DA nerve terminals. 5-HT release within $A_9$ DA nerve terminals was greater than within $A_{10}$ somatodendrites during movement behaviors.

The data suggest that 5-HT may control episodic and rhythmic movement behaviors in DA basal nuclei and in the brain stem nucleus, $A_{10}$ somatodendrites. This control or modulation is different in basal nuclei compared with the brain stem nucleus, $A_{10}$ somatodendrites.

Superior temporal resolution is a crucial component of technologies that claim to study neurotransmitters and behavior within the same animal and in real time.

Example 6

Cocaine Disrupts Normal Rhythmic, Episodic Modulation of Movement Via 5-HT in Motor Circuits Methods used in this example have been described (Broderick P A, 1995, U.S. Pat. No. 5,433,710; Broderick P A, 1996, EP 90914306.7; Broderick P A, 1999, U.S. Pat. No. 5,938,903; Broderick P A, 1989, Brain Res. 495:115–12 1; Broderick P A, 1989, Brain Res. 495:115–121; Broderick P A, 1988, Neurosci. Lett. 95:275–280; Broderick P A, 1990, Electroanalysis 2:241–245; Broderick P A, 1993, Pharmacol. Biochem. Behav. 46:973–984; Broderick P A, 2002, Handbook of Neurotoxicology, Vol. 2, Chapter 13; Broderick P A et al., 2000, Brain Res. 878:48–63). The dosage of cocaine used was 10 mg/kg ip.

Figure 10:
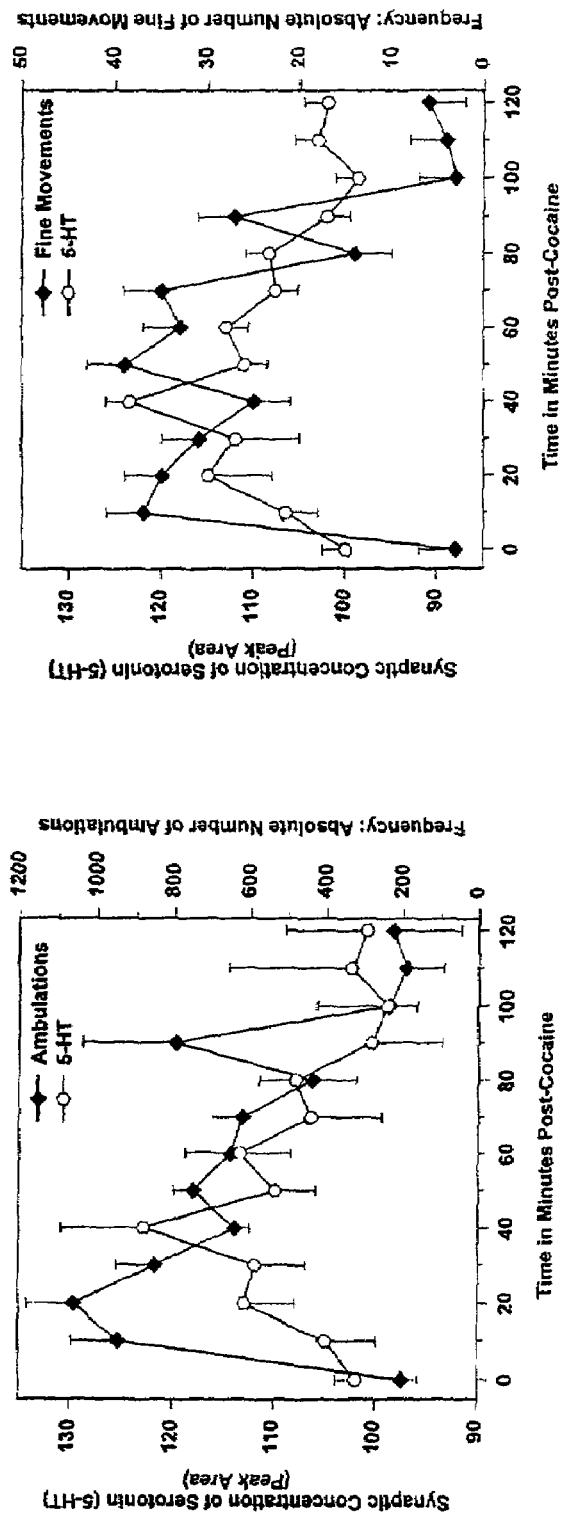
FIG. 10. Cocaine Neurochemistry and Behavior: Line graph depicting endogenous 5-HT release (open circles) at basal nucleus $A_{10}$ terminals, vlNAcc, in real time, while the freely moving, male, Sprague-Dawley laboratory rat is actually behaving, during cocaine-induced behavior (intraperitoneal injection of cocaine: two hour study). Serotonin, detected within seconds of release, is plotted with a line graph derived from simultaneous infrared photobeam monitoring of behavior (closed circles): locomotions (ambulations, left panel); stereotypy (fine movements, right panel). Open-field behaviors were studied in units of frequency of events, which were recorded every 100 ms during normal/ natural locomotor behavior. Data show that cocaine disrupted the normal episodic, rhythmic nature of locomotor and stereotypic movement which may be neuromodulated by 5-HT within the basal nucleus, $A_{10}$ terminals. Data suggest that cocaine caused neuroadaptive process in 5-HT mechanisms in DA basal nuclei.

The temporal synchrony between 5-HT release in basal nucleus $A_{10}$ terminals, v1NAcc, and movement behaviors is disrupted after cocaine administration. FIG. 10 shows the 5-HT response to cocaine, plotted with resulting ambulations (left panel) and fine movement (right panel) during the psychomotor effects of cocaine, as movement occurred (same animal control in real time). Comparing this figure with FIG. 8 reveals that normal communication between basal 5-HT release in NAcc and movement behaviors is disrupted by cocaine. Although 5-HT levels still increase after cocaine, rhythmic control of movement by 5-HT is no longer observable in either ambulatory (locomotor) or fine movement (stereotypic) behaviors. Moreover, the magnitude of the 5-HT increase after cocaine is significantly less than 5-HT released and observed during natural movement without cocaine. Cocaine-induced behaviors after habituation are still increased, but the behaviors seem to occur in a frequency similar to those frequencies usually observed in smaller, younger, animals.

Figure 11:
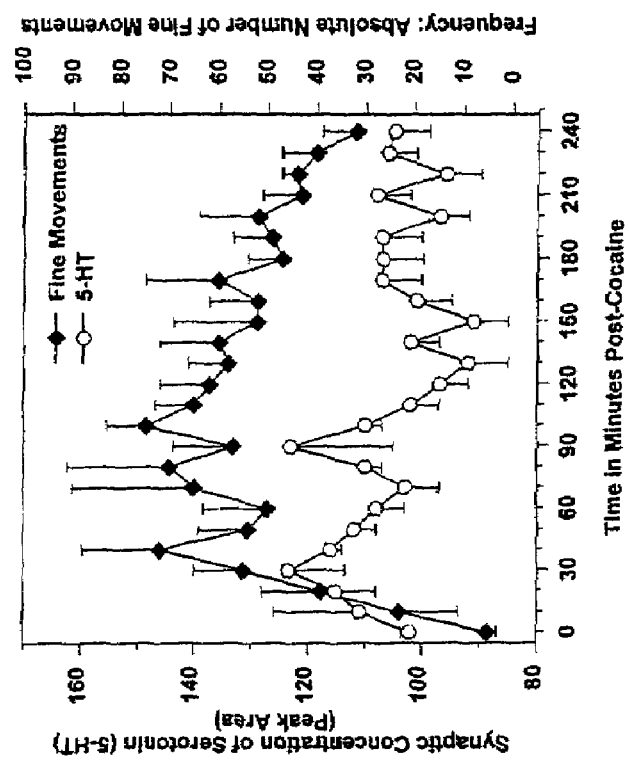
FIG. 11. Cocaine Neurochemistry and Behavior: Line graph depicting endogenous 5-HT release (open circles) at basal stem nucleus, DA $A_{10}$ somatodendrites, VTA, in real time, while the freely moving, male, Sprague-Dawley laboratory rat is actually behaving, during cocaine behavior (subcutaneous injection of cocaine: four hour study). Serotonin, detected within seconds of release, is plotted with a line graph derived from simultaneous infrared photobeam monitoring of behavior (closed circles): locomotion (ambulations, left panel); stereotypy (fine movements, right panel). Open-field behaviors were studied in units of frequency of events, which were recorded every 100 ms during normal/ natural locomotor behavior. Data show that cocaine disrupted the normal episodic, rhythmic nature of locomotor movement, likely by disturbing 5-HT neuromodulation of behavior in DA motor circuits and causing neuroadaptation.
Figure 11:
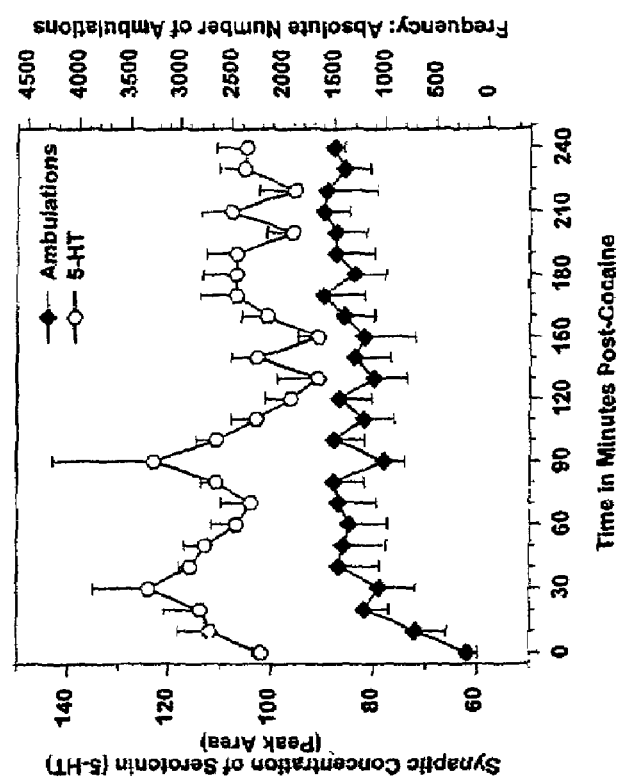

The temporal synchrony between 5-HT release in $A_{10}$ somatodendrites and movement behaviors is also disrupted after cocaine administration. Although VTA is not a basal nucleus, these DA cell bodies are a component of the mesocorticolimbic motor circuit. FIG. 11 shows the 5-HT response to cocaine, plotted with resulting ambulations (left panel) and fine movement (right panel) behaviors during the psychomotor effects of cocaine, as movement occurred (same animal control in real time). This figure shows that the previous normal/natural communication (shown in FIG. 9) between basal 5-HT release in $A_{10}$ somatodendrites and movement behaviors has been disrupted. The data show that enhanced 5-HT release in VTA after cocaine is no longer synchronous with movement behaviors. Thus, ambulations (locomotion) and fine movement behaviors of grooming and sniffing are not related temporally to 5-HT release at $A_{10}$ somatodendrites after cocaine. Serotonin release increased when compared with habituation behavior, but the magnitude of the increase was smaller than observed during normal movement without cocaine. Despite the rise in 5-HT levels, 5-HT does not direct normal, rhythmic episodic movements after cocaine administration.

The general trend of changes in 5-HT and movement behaviors observed here confirm previously reported results (Yeghiayan S K et al., 1997, Pharmacol. Biochem. Behav. 56:251–259). However, previous studies have not been able to detect these subtle changes nor have these previous studies been able to detect normal/natural episodic, rhythmic nature of locomotor (exploratory) movement or stereotypy, either in neurochemistry or behavior.

5-HT control or modulation of movement behaviors in $A_{10}$ basal nucleus and in $A_{10}$ somatodendrites during normal/natural movement behaviors is subsequently disrupted by cocaine. Even in the first thirty minutes after cocaine, the episodic rhythmic nature of locomotor (exploratory) movement behavior and stereotypic behavior has been disrupted.

5-HT release in basal nuclei and VTA DA somatodendrites after cocaine is greater than those during habituation but less than those seen during normal/natural movement behaviors.

Neuroadaptation cannot be determined by simply studying the general direction of the response of 5-HT to cocaine. Using Broderick probe microvoltammetry, neuroadaptative responses by 5-HT in motor circuits have been seen after a single injection of cocaine. The observed neuroadaptative response by 5-HT in motor circuits is independent of temperature changes since temperature was kept constant at 37.5±0.5° C. Neuroadaptation may be a predisposition to cocaine neurotoxicity.

In vivo microvoltammetric studies enable the detection of subtle changes necessary to see alterations in normal/natural neurochemistry and behavior that existed before the administration of cocaine. The studies show that neuronal damage to basal nuclei and brain stem nuclei may have occurred after the administration of cocaine.

Superior temporal resolution is a crucial component of technologies that claim to study neurotransmitters and behavior within the same animal and in real time.

Example 7

CPG'S Within Basal Nuclei May Induce Rhythmic Movement by 5-HT

The following provides a rationale for studies using CPG's to explain how brain and spinal cord injuries can come about. The following also describes the necessity for neurotransmitters and movement, behavior or otherwise to be synchronous. The invention further provides methods for diagnosing injury where the patterns are asynchronous.

To date, there have been no reports of 5-HT modulation that is intrinsic to CPG's that operate rhythmic locomotion or stereotypy in basal nuclei. Yet, basal nuclei are known to be involved in the development of automaticity and to play a primary role in both movement preparation and execution, possibly by optimizing muscular activity patterns once a motor decision has been made (Brooks D J, 1996, Basal Ganglia function during normal and Parkinsonian movement, PET activation studies. In Advances in Neurology (Battistin, L. Scarlato, G., Caraceni, T. and Ruggieri, S. Eds.), Lippincott-Raven, Phil., Pa. pp. 433–441).

Studies of neurotransmitters in basal nuclei and brain stem nuclei have typically focused on DA. For example, it is known that the basic rhythm for locomotion is generated centrally in spinal networks. The transition from stance to swing is regulated by afferent signals from leg flexor and extensor muscles. These afferent signals are ultimately influenced in intensity and pattern by descending signals from CNS neuronal circuitry (Pearson K et al., 2000, Principles of Neural Science, 4th edition, pp. 738–755). Again, the catecholamines have taken preference as targets for study. Landmark studies, performed about thirty years ago, showed that injection of the catecholaminergic drugs, L-DOPA and nialamide, into spinal cord generated spontaneous locomotor activity (Jankowska E et al., 1967, Acta Physiol. Scand. 70:369–388; Jankowska E et al., 1967, Acta Physiol. Scand. 70:389–402).

Moreover, electrophysiological studies of DA in the basal nucleus, DStr, have shown that DA neurons operate in bursts of action potentials that increase bursting and change bursting patterns when 96% DA neurons are damaged (Hollermann J R et al., 1990, Brain Res. 533:203–212). Other electrophysiological studies have shown that the excitotoxin, kainic acid, when injected into the basal nucleus, DStr, changed the pattern of the normal neuronal rhythm in the basal stem nucleus, substantia nigra (SN). Since SN usually exhibits a slow rhythmic firing of action potentials, damage to the neurons has been reported to cause a disorganized rhythm. This SN model has been used as an animal model to study the movement disorder, Huntington's Disease (Doudet D et al., 1984, Brain Res. 302:45–55). Therefore, empirical precedents provide evidence for a clear association between DA, neuronal damage, and disorganized rhythms, at least from electrophysiological studies.

The instant invention provides a novel approach of examining the involvement of 5-HT modulation in the functioning of CPG's that operate rhythmic locomotion or stereotypy in basal nuclei. The technology presented here, provides a way to concurrently study 5-HT release in basal nuclei, movement circuits, and behavior, in an animal or human. The analysis may further include observing changes in one or more of these three factors upon exposure to some stimulus.

The empirical evidence presented in the Examples suggests that (a) 5-HT in basal nuclei may be responsible, at least in part, for the normal/natural episodic, rhythmicity known to exist with locomotor and stereotypic movements and (b) a subtle neuroadaptation is caused by cocaine between 5-HT and cocaine-induced movements known as "psychotic behavior" by a single or multiple CPG network. Interestingly, neuroadaptation, induced by cocaine is highly time-dependent. This is consistent with the observation that neuromodulatory inputs can reconfigure CPG networks to produce specific motor output patterns (Kiehn O et al., 1996, J. Neurophysiol. 75:1472–1482).

Thus, cocaine may act through a time-dependent, 5-HT CPG neuronal network to cause neuroadaptation to occur which may lead to cocaine neurotoxicity. This cocaine-5-HT driven neuroadaptation may reflect neuronal damage and may be a marker for cocaine neurotoxicity.

Locomotor (exploratory) activity and stereotypic behaviors are episodic and rhythmic although they are commonly not described as such. FIGS. 7 through 9 depict the episodic, rhythmicity seen in normal/natural movement behaviors. Neuromodulation by the biogenic amine, 5-HT, within basal nuclei and $A_{10}$ brain stem nucleus is depicted as these movements occur and as these movements are presumably controlled, directed, modulated or regulated by 5-HT.

Hyperactive locomotion and stereotypic behaviors are often thought of and referred to as psychomotor stimulant behaviors. Also, repetitive behaviors induced by cocaine have been perceived as "meaningless" or goalless behaviors. It has been said that the term "stereotypy" applies to a behavioral act that is repeated again and again, but, unlike a motivational act, it makes no sense because it does not achieve an adaptive outcome (Teitelbaum P, Pellis S M, and De Vietti T L, 1990, Disintegration into sterotypy induced by drugs of brain damage: a microdescriptive behavioral analysis. In: Neurobiology of Steroryped Behavior (Cooper S J and Dourish C T Eds.), Oxford Univ. Press, NY. pp. 169–199.). However, repetitive behaviors produced by cocaine may not be meaningless or non-adaptive. Rather, neuroadaptation to cocaine, possibly leading to habit-forming behavior, may be the unfortunate maladaptive outcome. FIGS. 10 and 11 show that cocaine disrupted the normal episodic rhythm of natural movement; cocaine caused normal rhythmic movement to be disorganized.

It is interesting that the concept of "rhythm" in normal open-field movement is virtually ignored or forgotten when one studies the literature on the mechanism of action of cocaine. Conceptually, when neuroscientists speak of cocaine-induced psychomotor stimulant behavior, it seems as if movement does not occur until cocaine is administered or injected. The Examples herein illustrate that there are actually greater enhancements in 5-HT during movement before cocaine administration than in the same animal after cocaine administration. In addition, cocaine-induced movement was not significantly increased over movement without cocaine.

Example 8

Schizophrenia

The first evidence that schizophrenia may be associated with 5-HTergic abnormalities was the observation that there was a structural similarity between 5-HT and the hallucinogenic drug, lysergic acid diethylamide (LSD) (Gaddum J H, 1954, Ciba Foundation Symposium on Hypertension, pp. 75–77; Wooley D W et al., 1954, PNAS 40: 228–231). Solomon Snyder (Snyder S H, 1972, Arch. Gen. Psychiat. 45:789–796) reported, however, that the psychosis induced by LSD in humans exhibited a vastly different symptomatology that than of schizophrenic-induced psychosis. A revival of interest in the relationship between 5-HT and schizophrenia occurred about fifteen years ago, when the atypical neuroleptic was found to have a high affinity for 5-$HT_2$ receptors (Altar C A et al., 1986, Brain Res. Bull. 16:517–525). Also, clozapine was found to be particularly effective in treating patients intractable to other neuroleptics and clozapine was found to produce less extrapyramidal side effects (EPS) (movement disorders) than did other previous neuroleptics (Kane J et al., 1988, Arch. Gen. Psychiat. 45:789–796; Tamminga C A et al., 1987, Psychopharmacology: the Third Generation of Progress, pp. 1129–1140).

A mediation for 5-HT in either the disease of schizophrenia itself or in the movement disorders known to be caused by the classical neuroleptics remains under study; two excellent reviews are published (Iqbal N et al., 1995, Eur. Neuropsychopharmacol. 5(Suppl.):11–23; Abi D A et al., 1977, J. Neuropsychiat. Clin. Neurosci. 9:1–17). Nonetheless, a current hypothesis derived from human and animal studies regarding this atypical neuroleptic is that clozapine acts via its 5-$HT_2$ antagonistic effect to alleviate movement disorders in psychosis. Furthermore, in treating the schizophrenic psychotic abnormality via its $DAD_2$ antagonistic receptor action, the drug produces less EPS than its classical counterparts, via 5-HT (Meltzer H Y, 1989, Psychopharmacology 99(Suppl.):18–27; Broderick P A et al., 1998, J. Neural. Transm. 105:749–767; Hope O., Lineen, E., Okonji, C., Green, S., Saleem, A., Aulakh, C. S. and Broderick, P. A., 1995, Cocaine has remarkable nucleus accumbens effects on line, with behavior in the serotonin-deficient Fawn Hooded rat. NIH/NIGMS Symposium, Washington, D.C; Wadenburg M L, 1996, Neurosci. Biobehav. Rev. 20:325–329; Kapur S et al., 1996, Am. J. Psychiat. 153(4):466–476;

Martin P, 1998, 5-HT2 Receptor Antagonism and Antipsychotic Drugs; A Behavioral and Neurochemical Study in a Rodent Hypoglutamatergia Model. PhD. Thesis, Goteborg Univ., Sweden, pp. 1–64) and possibly by its $DAD_4$ action (Van Tol HHM et al., 1991, Nature 350:610–614). Perhaps the present data can lend an explanatory note to a fairly recent study in which the classical $DAD_2$ receptor antagonist, haloperidol, was shown to induce the movement dysfunction, catalepsy, by 5-HTergic mediation (Neal-Beliveau B S et al., 1993, J. Pharmacol. Exp. Therap. 265:207–217).

Example 9

Conclusion

Serotonin release from DA $A_9$ and $A_{10}$ basal nuclei and $A_{10}$ brain stem nuclei may be regulated by a 5-HT-regulated CPG, presumably originating from raphe somatodendrites based on empirical studies using in vivo microvoltammetry with Broderick probe microelectrodes. Animals exhibited repetitive, episodic and rhythmic normal/natural movements, influenced by 5-HT within DA $A_9$ and $A_{10}$ neural circuits without any drug treatment. Furthermore, cocaine disrupted such normal/natural episodic rhythmic movement by altering release of 5-HT, precisely within the DA basal nuclei that are responsible for controlling voluntary movement. A further disruption of normal, episodic rhythmic movement by 5-HT after cocaine occurred in the brain stem nucleus, VTA, the cell bodies for the basal nucleus, NAcc. Thus, 5-HT neuroadaptation by cocaine may be a predisposition or marker for cocaine induced neuronal damage or neurotoxicity. Implications for the study of other movement disorders, like spinal cord injury, through these empirical data, are noteworthy.

REFERENCES

The references cited throughout this application and listed on the attached Form 1449 are all incorporated herein in their entirety by reference.

We claim:

1. A method of diagnosing and/or monitoring a neurological disorder in a mammal comprising:
    generating a temporally and/or spatially resolved Broderick probe microvoltammogram of said mammal;
    determining from said microvoltammogram the presence and concentration of a marker selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide; and
    comparing said marker concentration to a threshold value of said respective marker, wherein said threshold value is derived from a Broderick probe microvoltammogram of a mammal that does not have said neurological disorder, wherein the concentration of said marker differs from said threshold value, and wherein said neurological disorder is selected from the group consisting of athetoid, dystonic diseases, epilepsy, Lesch-Nyhan disease, disorders of the basal ganglia, white matter disease, cerebral hemorrhage, head trauma, multiple sclerosis, central nervous system infection, hydrocephalus, and Leukodystrophies.

2. The method of claim 1 wherein the epilepsy is temporal lobe epilepsy.

3. A method of monitoring a controlled-substance treatment in a mammal having a neurological disorder comprising:
    generating a temporally and/or spatially resolved Broderick probe microvoltammogram of said mammal:
    determining from said microvoltammogram the presence and concentration of a marker selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide; and
    comparing said marker concentration to a threshold value of said respective marker,
    wherein said threshold value is derived from a Broderick probe microvoltammogram of a mammal that does not have said neurological disorder, wherein the concentration of said marker differs from said threshold value wherein the controlled substance treatment is a treatment selected from the group consisting of opiates, stimulants, and depressants, wherein the opiate is selected from the group consisting of alfentanil, aiphaprodine, anileridine, apomorphine, bezitramide, carfentanil, cocaine, codeine, 4-cyano-2-dimethylamino-4,4-diphenyl butane, 4-cyano-1-methyl-4-phenylpiperidine pethidine-intermediate-B, dextropropoxyphene, dextrorphan, dihydrocodeine, dihydroetorphine, diphenoxylate, 1-diphenylpropane-carboxylic acid pethidine (meperidine), ecgonine, ethyl-4-phenylpiperidine-4-carboxylate pethidine-intermediate-C, ethylmorphine, etorphine hydrochloride, fentanyl, hydrocodone, hydromorphone, isomethadone, levo-alphacetyl-methadol, levomethorphan, levorphanol, metazocine, methadone, methadone-intermediate, 2-methyl-3-morpholino- 1,1-methyl-4-phenylpiperidine-4-carboxylic acid, metopon, morphine, moramide-intermediate, nalbuphine, nalmefene, naloxone, naltrexone, opium, oxycodone, oxymorphone, pethidine-intermediate-A, phenanthrene alkaloid-sphenazocine, piminodine, racemethorphan, racemorphan, remifentanil, sufentanil, thebaine, and the baine-derived butorphanol.

4. A method for distinguishing a gray matter tissue from a white matter tissue comprising:
    generating a temporally and/or spatially resolved Broderick probe microvoltammogram of the tissue;
    determining from said microvoltammogram the presence and concentration of a marker selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide; and
    comparing said marker to a threshold value of said respective marker,
    wherein said threshold value is derived from a Broderick probe microvoltammograms of a gray matter tissue selected from the group consisting of neocortical gray, pyramidal layers, and granular cells of the dentate gyrus and
    a white matter tissue selected from the group consisting of temporal stem, alveus, subiculum, and band of baillarger and wherein said step of comparing said marker concentrations distinguishes whether said tissue is gray matter or white matter.

5. A method of measuring the neurotoxicity of a substance comprising:
comparing a temporally and/or spatially resolved Broderick probe microvoltammogram of neural tissue in the absence of said substance with a temporally resolved Broderick probe microvoltammogram of tissue in the presence of said substance, wherein said substance is selected from the group consisting of opiates, stimulants, depressants, hallucinogens, anti-tumor chemicals, anti-depressants, and antiepileptic chemicals.

6. The method of claim 5 wherein said substance is a pharmaceutical or a pharmaceutical candidate.

7. The method of claim 6 wherein said pharmaceutical has antitumor activity against at least one tumor or cancer cell line.

8. The method of claim 7 wherein said substance is cocaine.

9. The method of claim 6 wherein said substance is selected from the group consisting of minerals, ions, metals, caffeine, ethanol, nicotine, and cannabinoids.

10. The method of claim 6 wherein said substance is selected from the group consisting of proteins, lipids, nucleic acids, carbohydrates, glycolipids and lipoproteins.

11. A method of treating temporal lobe epilepsy comprising:
generating a temporally and/or spatially resolved Broderick probe microvoltammogram of a temporal lobe tissue of a subject in need of such treatment; comparing said microvoltammogram to at least one reference Broderick probe microvoltammogram;
determining the type and extent of temporal lobe resection necessary to achieve a substantially seizure free outcome; and
resecting the subject's temporal lobe accordingly; wherein said reference microvoltammogram is a Broderick probe microvoltammogram of the corresponding non-epileptogenic temporal lobe tissue of said subject if the subject is human or a non-human mammal having mesial temporal lobe epilepsy or neocortical temporal lobe epilepsy.

12. The method of claim 11 wherein said generating step further comprises simultaneously monitoring or recording a second parameter.

13. The method of claim 12 wherein said second parameter is selected from the group consisting of a movement behavior, a cognitive function, subject's consciousness, and the presence and the concentration of a drug, protein, nucleic acid, carbohydrate, or lipid.

14. A method for determining the grade of a tumor (degree of malignancy) comprising:
generating a temporally and/or spatially resolved Broderick probe microvoltammogram of a test tissue;
determining from said microvoltammogram the presence and concentration of at least two markers selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide; and
comparing said test tissue marker concentrations to threshold values of the markers wherein, said threshold values are derived from Broderick probe microvoltammogram(s) of reference tissue selected from the group consisting of non-cancerous tissue and cancerous tissue.

15. A method for continuous or intermittent therapeutic monitoring of pharmacologic and nonpharmacologic therapies for brain disorders comprising:
contacting a brain tissue having a brain disorder selected from the group consisting of disorders of the basal ganglia, epilepsy, multiple sclerosis, bipolar disorder, subarachnoid hemorrhage, hydrocephalus, cerebral infarction, autoimmune disorders and infections of the central nervous system with a Broderick probe;
administering a pharmacologic and nonpharmacologic therapy;
applying a potential to said Broderick probe; and
generating a temporally and/or spatially resolved Broderick probe microvoltammogram.

16. The method of claim 15 wherein the; disorder is epilepsy.

17. The method of claim 15 wherein the disorder in monitored continuously.

18. The method of claim 15 wherein the disorder is monitored intermittently.

19. A method for detecting a site of nerve damage or blockage in a mammal comprising:
contacting a central pattern generator neural network with a Broderick probe;
applying a potential to said Broderick probe;
generating a temporally and/or spatially resolved Broderick probe microvoltammogram of said central pattern generator neural network;
simultaneously monitoring movement behavior of said mammal; and
comparing said microvoltammogram and movement behavior to a reference microvoltammogram and concurrent movement behavior of a mammal that does not have nerve damage or blockage, wherein said step of comparing distinguishes synchrony and/or asynchrony between neurotransmitter in the central pattern generator and movement and indicates nerve damage or blockage, wherein said neurotransmitter is selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide.

20. A method for diagnosing brain or spinal cord injury in a mammal comprising:
contacting a central pattern generator neural network with a Broderick probe;
applying a potential to said Broderick probe;
generating a temporally and/or spatially resolved Broderick probe microvoltammogram of said central pattern generator neural network;
simultaneously monitoring movement behavior of said mammal; and
comparing said microvoltammogram and movement behavior to a reference microvoltammogram and concurrent movement behavior of a mammal that does not have brain or spinal cord injury; wherein said comparing step distinguishes synchrony and/or asynchrony between neurotransmitter in the central pattern generator and movement and indicates brain or spinal cord injury, wherein said neurotransmitter is selected from the group consisting of serotonin, dopamine, ascorbic acid, norepinephrine, γ-aminobutyric acid, glutamate, neurotensin, somatostatin, dynorphin, homovanillic acid, uric acid, tryptophan, tyrosine, nitrous oxide, and nitric oxide.

* * * * *